(12) United States Patent
Yamamoto et al.

(10) Patent No.: US 10,022,389 B2
(45) Date of Patent: Jul. 17, 2018

(54) PROPHYLACTIC OR THERAPEUTIC DRUG FOR CONSTIPATION

(71) Applicant: TAISHO PHARMACEUTICAL CO., LTD., Tokyo (JP)

(72) Inventors: Daisuke Yamamoto, Tokyo (JP); Fusayo Io, Tokyo (JP); Koji Yamamoto, Tokyo (JP)

(73) Assignee: TAISHO PHARMACEUTICAL CO., LTD., Tokyo (JP)

(*) Notice: Subject to any disclaimer, the term of this patent is extended or adjusted under 35 U.S.C. 154(b) by 55 days.

(21) Appl. No.: 14/765,134

(22) PCT Filed: Feb. 3, 2014

(86) PCT No.: PCT/JP2014/052465
§ 371 (c)(1),
(2) Date: Jul. 31, 2015

(87) PCT Pub. No.: WO2014/119787
PCT Pub. Date: Aug. 7, 2014

(65) Prior Publication Data
US 2015/0374735 A1    Dec. 31, 2015

(30) Foreign Application Priority Data

Feb. 4, 2013   (JP) ................. 2013-019754

(51) Int. Cl.
*A61K 31/7034*   (2006.01)
*A61K 31/351*    (2006.01)
*C07D 309/10*    (2006.01)
*A61K 9/16*      (2006.01)
*A61K 9/20*      (2006.01)

(52) U.S. Cl.
CPC ........ *A61K 31/7034* (2013.01); *A61K 9/1652* (2013.01); *A61K 9/2059* (2013.01); *A61K 31/351* (2013.01); *C07D 309/10* (2013.01)

(58) Field of Classification Search
CPC .............. A61K 31/351; A61K 31/7034; A61K 9/2059; A61K 9/1652; C07D 309/10
USPC ......................................................... 514/35
See application file for complete search history.

(56) References Cited

U.S. PATENT DOCUMENTS

| | | | | |
|---|---|---|---|---|
| 8,466,113 B2 * | 6/2013 | Kakinuma | ........... | C07D 309/10 514/23 |
| 2011/0306759 A1 | 12/2011 | Kakinuma et al. | | |
| 2013/0085132 A1 * | 4/2013 | Miura | ............. | C07D 401/12 514/212.08 |
| 2013/0144050 A1 | 6/2013 | Kimura et al. | | |
| 2015/0141631 A1 | 5/2015 | Isaji et al. | | |

FOREIGN PATENT DOCUMENTS

| | | |
|---|---|---|
| DE | 2830424 A1 | 1/1980 |
| GB | 2 447 067 A | 9/2008 |
| JP | 2012-518631 A | 8/2012 |
| RU | 2161033 C2 | 12/2000 |
| RU | 2015123738 A | 1/2017 |
| WO | WO 97/06808 | 2/1997 |
| WO | 2006025599 A1 | 3/2006 |
| WO | WO 2007/136116 A2 | 11/2007 |
| WO | WO 2010/095768 A1 * | 8/2010 ........... C07D 309/10 |
| WO | 2012/023598 A1 | 2/2012 |
| WO | 2013/031922 A1 | 3/2013 |
| WO | 2013/168671 A1 | 11/2013 |
| WO | WO 2014/081660 A1 | 5/2014 |

OTHER PUBLICATIONS

Communication dated May 19, 2016 from the European Patent Office in counterpart application No. 14746685.8.
Masanori Fukushima, The Merck Manual 17$^{th}$ Japanese edition, Nikkei Business Publications, Inc., Dec. 1999, pp. 280-286.
Yakuji, The Pharmaceuticals Monthly, vol. 51, No. 9, Sep. 2009, pp. 127-132.
Haneda et al., "Sodium glucose cotransporter1 (SGLT-1 ) no Hatsugen kara Mita Hito Daicho Zentekishutsugo ni Okeru Suiyoben no Hassho Kijo" Journal of the Japanese Society of Gastroenterology, vol. 102, Extra Edition, 2005, p. A238.
An International Preliminary Report on Patentability dated Aug. 4, 2015, which issued during the prosecution of Applicant's PCT/JP2014/052465.
Communication dated May 12, 2015 from the Japanese Patent Office in counterpart application No. 2014-526017.
An International Search Report dated Apr. 28, 2014, which issued during the prosecution of Applicant's PCT/JP2014/052465.
Communication dated Jan. 16, 2017, from the Intellectual Property Office of Taiwan in corresponding application No. 103103751.

(Continued)

*Primary Examiner* — Ganapathy Krishnan
(74) *Attorney, Agent, or Firm* — Finnegan, Henderson, Farabow, Garrett & Dunner, L.L.P.

(57) ABSTRACT

New drugs useful in the prevention or treatment of constipation are provided, in which SGLT1 inhibiting compounds, in particular, a 4-isopropylphenyl glucitol compound represented by the following formula (I), or pharmaceutically acceptable salts thereof are contained as an active ingredient:

[Formula 1]

(I)

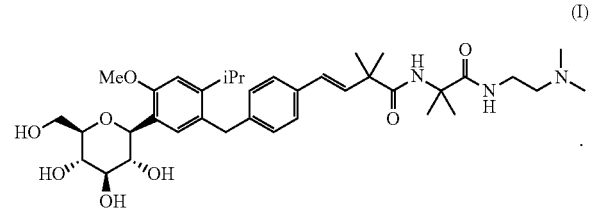

2 Claims, 2 Drawing Sheets

(56) References Cited

OTHER PUBLICATIONS

Nobuya Inagaki, "Role of sodium-glucose transporters in glucose uptake of the intestine and kidney," Journal of Diabetes Investigation, vol. 3, 2012, p. 352-353.
Loo et al., "Cotransport of water by the $Na^+$/glucose cotransporter," Proc. Natl. Acad. Sci. USA, 1996, 93: 13367-13370.
Lam et al., "Missense mutations in SGLT1 cause glucose-galactose malabsorption by trafficking defects," Biochimica et Biophysica Acta, 1999, 1453: 297-303.
Office Action dated Aug. 8, 2017, issued in corresponding Singapore Patent Application No. 10201700267P, 10 pages.
Abstract of Lostao et al., "Phenylglucosides and the Na+/glucose cotransporter (SGLT1): analysis of Interactions," J. Membr. Biol., 1994, 142(2):161-170, 1 page.
Office Action dated Sep. 4, 2017, issued in corresponding Russian Patent Application No. 2015137671/15, 6 pages.
English translation of Office Action dated Sep. 4, 2017, issued in corresponding Russian Patent Application No. 2015137671/15, 3 pages.
Decision to Grant issued in corresponding Russian Patent Application No. 2015137671/15, dated Jan. 9, 2018, 11 pages.

* cited by examiner

\#\#\#; p<0.001 (Welch's test) versus normal group
\*\*; p<0.01 (Dunnett-type rank sum test) versus vehicle group \*; p<0.05, \*\*\*; p<0.001 (Dunnett-type rank sum test) versus vehicle group \#\#\#; p<0.001 (Welch's test) versus normal group
*; p<0.05, **; p<0.01 (Dunnett-type rank sum test) versus vehicle group

*; p<0.05 (Dunnett's test) versus vehicle group

PROPHYLACTIC OR THERAPEUTIC DRUG FOR CONSTIPATION

CROSS REFERENCE TO RELATED APPLICATIONS

This application is a National Stage of International Application No. PCT/JP2014/052465 filed Feb. 3, 2014, claiming priority based on Japanese Patent Application No. 2013-019754 filed Feb. 4, 2013, the contents of all of which are incorporated herein by reference in their entirety.

TECHNICAL FIELD

The present invention relates to a prophylactic or therapeutic drug for constipation and, more specifically, to a prophylactic or therapeutic drug for constipation comprising as an active ingredient a compound that inhibits sodium-dependent glucose cotransporter 1 (hereinafter sometimes referred to as SGLT1).

BACKGROUND ART

Constipation refers to conditions where the number of bowel movements and the amount of stools decrease so much that the process of defecation involves pains or difficulties. On account of changes in eating habit, insufficient exercise, a time-bound and stressful social life, and the increasing population of the elderly, the frequency of constipation is presumably increasing.

Under normal conditions, food taken into the mouth is digested and absorbed, leaving undigested waste material as the bowel contents, which are then forwarded from the small to the large intestine. In the large intestine, the waste material solidifies as water is absorbed and in the process of its peristaltic movement toward the anus, it arrives at the sigmoid colon, where it is stored as stools. When the stools are propelled into the rectum by a contracting motion called mass peristalsis, the walls of the rectum stretch, signaling a stimulation that is conducted to the defecatory center in the spinal cord and a defecatory reflex takes place, causing the anal sphincter muscles to relax and the rectum to contract. Simultaneously, the cerebrum recognizes the urgency to pass stools and the abdominal pressure is increased voluntarily to initiate defecation. Components of constipation reportedly include decreased autonomic nerve, motility or defecatory reflex functions in the lower digestive tract, excessive water absorption in the intestinal tract, decreased secretion of intestinal juice, etc.

Major known cases of constipation include, for example, functional constipation, organic constipation, symptomatic constipation, and drug-induced constipation. Functional constipation is known to include, for example, transient simple constipation, atonic constipation due to decreased peristalsis of the large intestine, spasmodic constipation due to hypertonia of the colon mediated by the autonomic nerves, and rectal constipation due to weak defecatory reflex upon the arrival of stools in the rectum. Organic constipation is caused by obstruction or constriction of the intestinal tract due to underlying diseases in or around the intestinal tract. Symptomatic constipation is part of the symptoms of underlying diseases such as metabolic, endocrine, nerve, and myopathic diseases. Medicaments that are known to cause drug-induced constipation include psychotropic or antidepressant agents having an anti-cholinergic action, narcotics such as morphine, and vinca alkaloids as anticancer agents.

Constipation also occurs as an abnormal bowel movement in irritable bowel syndrome that involves abdominal discomfort or pain which lightens or disappears upon defecation. The elderly often complain of constipation associated with physiological changes due to the aging intestinal tract. Constipation is more common in women than in men because, for one thing, they have their own physical characteristic features such as weak abdominal muscles and, for another, they are subject to hormonal actions during the menstrual cycle. Pregnant women, too, complain of constipation due to hormonal actions and various other effects including compression of the intestinal tract, decreased motility of the diaphragm, and weakened abdominal muscles. Constipation also occurs as a somatic symptom of mental diseases such as depression and anxiety neurosis (Non-Patent Documents 1 and 2).

Medicaments used for constipation include: osmotic laxatives classified to be salt laxatives such as magnesium oxide or saccharide laxatives such as D-sorbitol; bulk-forming laxatives such as polycarbophil calcium; stimulant laxatives such as sennosides; and infiltrating laxatives such as dioctyl sodium sulfosuccinate. Also used are 5-hydroxytryptamine 4 (5-HT4) receptor agonists such as prucalopride, and type 2 chloride channel (ClC-2) agonists such as lubiprostone. Glycerin is one of the medicaments used as enemas.

Medical therapy of constipation starts with the use of salt or bulk-forming laxatives. The salt laxative magnesium oxide requires precautions to be taken against hypermagnesemia, particularly when they are used in the elderly or in patients with renal disorder. The bulk-forming laxative polycarbophil calcium is mild in action, taking time for the efficacy to develop. If these medicines prove inefficacious, stimulant laxatives are attempted. Stimulant laxatives act on the nerve plexus in the large intestinal tract to enhance peristalsis but upon prolonged use, they become addictive, causing atrophy of the nerve plexus to exacerbate the relaxation of the large intestine. The use of stimulant laxatives is limited to the smallest possible amount and the shortest possible period. Therefore, a therapeutic for constipation that is safer and more efficacious with less side effects which, although being mild in action, can rapidly develop its efficacy is expected to benefit many patients. As a further problem, stimulant laxatives have a mucosa irritating action, so if dissolved in the stomach or degraded with gastric acid, the mucosa of the stomach is irritated causing various side effects such as severe stomach pain, nausea, and vomiting; it is therefore recommended that stimulant laxatives be used as suppository. Hence, it is desired that even upon oral administration which is convenient and the most desirable, medicaments are preferably free of the side effect issue and that the active ingredient remains chemically stable and unaffected by metabolism as it passes through the strongly acidic stomach and then through the neutral bowels until it exhibits its efficacy in the target site bowel.

Now, sodium-dependent glucose cotransporter 1 (SGLT1) is a sodium cotransporter that is mainly found in epithelial cells in the small intestine and which is responsible for the absorption of glucose and galactose which result from the digestion of carbohydrates contained in meals. Since compounds that inhibit the SGLT1 existing in the small intestine suppress the absorption of saccharides, they are considered to be useful as hypoglycemic drugs, therapeutics for diabetes mellitus or as therapeutics for obesity, and efforts are being made to develop such pharmaceuticals. Compounds so far reported to be capable of suppressing SGLT1 include DSP-3235 (KGA-2727 or GSK1614235) (Patent Document 1), SAR474832 (Non-Patent Document 3), and LX4211

(Patent Document 2), as well as several other compounds (Patent Documents 3 and 4). However, none of these SGLT1 inhibiting compounds are known to be effective in preventing or treating constipation.

CITATION LIST

Patent Literature

Patent Document 1: International Publication WO2004/018491
Patent Document 2: International Publication WO2008/042688
Patent Document 3: International Publication WO2010/095768
Patent Document 4: International Publication WO2012/023598.

Non-Patent Literature

Non-Patent Document 1: medicina, 2012, 49(2), 199-202
Non-Patent Document 2: Supplementary Volume of *Nippon Rinsho*, New Syndrome by Area Series, No. 12, "*Shoukakan Shoukougun* (Digestive Tract Syndrome) (Vol. 2 in two volumes)", 2009, 422-427
Non-Patent Document 3: 49th Annu. Meet. Soc. Toxicol. (March 7-11, Salt Lake City) 2010, Abst 2100.

SUMMARY OF INVENTION

Technical Problems

An object of the present invention is to provide a new drug useful in the prevention or treatment of constipation.

Another object of the present invention is to provide a drug for constipation that is safer and more efficacious with less side effects which, although being mild in action, can rapidly develop its efficacy.

Still another object of the present invention is to provide a drug for constipation which, even if administered orally, is free of the side effect issue and in which the active ingredient remains chemically stable and unaffected by metabolism as it passes through the strongly acidic stomach and then through the neutral bowels until it exhibits its efficacy in the target site bowel.

Solution to Problem

The present inventors conducted intensive studies with a view to attaining the above-mentioned objects and found, as a result, that SGLT1 inhibiting compounds, in particular, a 4-isopropylphenyl glucitol compound represented by the following formula (I) have a superior action for ameliorating constipation. The present inventors also found that the 4-isopropylphenyl glucitol compound represented by formula (I), being chemically stable and unaffected by metabolism in the digestive tract environment comprising the stomach through the small intestine, rapidly exhibited its efficacy in small enough amounts; the inventors further found that since the compound of formula (I) exhibited its efficacy while undergoing little absorption in vivo from the small intestine, it exerted less side effects even when they were used in more-than-effective amounts.

Hence, the present invention provides:

(1) A prophylactic or therapeutic drug for constipation comprising an SGLT1 inhibiting compound or a pharmaceutically acceptable salt thereof as an active ingredient.
(2) The prophylactic or therapeutic drug for constipation according to (1), wherein the SGLT1 inhibiting compound is a 4-isopropylphenyl glucitol compound represented by the following formula (I):

[Formula 1]

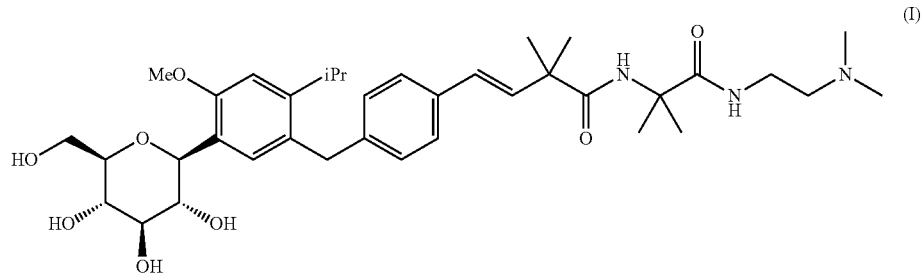

(I)

Advantageous Effects of Invention

The present invention has made it possible to provide a superior prophylactic or therapeutic drug for constipation that comprises a SGLT1 inhibiting compound as an active ingredient. The 4-isopropylphenyl glucitol compound represented by formula (I) can provide a drug for constipation that is safer and more efficacious with less side effects since it is mild in action and yet develops its efficacy rapidly. In addition, the 4-isopropylphenyl glucitol compound represented by formula (I), even if administered orally, is free of the side effect issue and the active ingredient remains chemically stable and unaffected by metabolism as it passes through the strongly acidic stomach and then through the neutral bowels until it exhibits its efficacy in the target site bowel.

DESCRIPTION OF EMBODIMENTS

Figure 1:
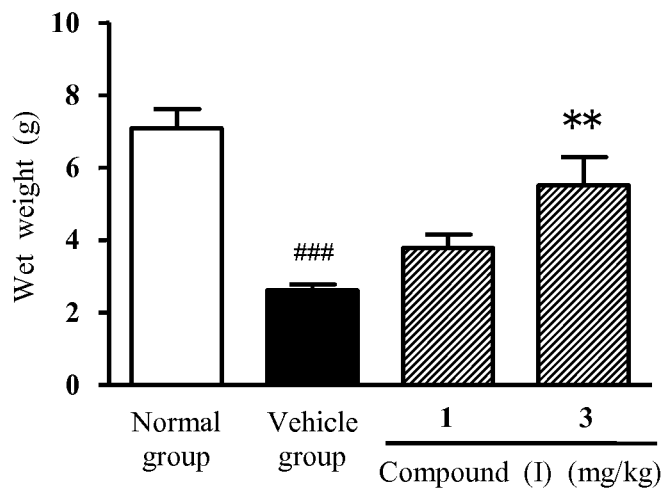
FIG. 1 is a diagram illustrating how well the constipation in rats as a constipation model was ameliorated (the wet weight of stools increased) as the result of administering the compound represented by formula (I).

On the following pages, the present invention is described in detail while explaining the significances of the symbols, terms and the like which are used in the specification of the subject application but it should be understood that the present invention is in no way limited to the modes illustrated below.

The term "prophylactic or therapeutic drug for constipation" as used herein refers to a pharmaceutical for ameliorating constipation which is used to promote defecation or bowel movements.

The term "constipation" as used herein refers to symptoms where the number of bowel movements and the amount of stools decrease so much that the process of defecation involves pains or difficulties; constipation includes a variety of cases that are manifested either acutely or chronically, organic, symptomatic, and drug-induced constipations. Also included are, for example, constipation in irritable bowel syndrome, constipation associated with physiological changes in the elderly due to the aging intestinal tract, constipation in women due, for example, to hormonal actions during the menstruation cycle, constipation in pregnant women, and constipation as a somatic symptom to a mental illness such as depression or anxiety neurosis. In certain cases, a bowel movement takes place but a sense of incomplete defecation (stools are not completely passed) or discomfort (e.g., bloating) is felt; even these conditions are included by the term "constipation." In addition, the use of the "prophylactic or therapeutic drug for constipation" according to the present invention is not limited to the prevention or treatment of the various cases of constipation mentioned above and they may also be used as defecation promoting pharmaceuticals for various purposes, e.g. emptying the intestinal tract during digestive tract examination or both before and after abdominal surgery, assisting in defecation after surgery, or promoting defecation after dosing of a contrast medium. Use may also be possible as medicaments for emptying the digestive tract of harmful materials such as undigested materials or toxic substances. Further use may also be possible as medicaments for promoting defecation in those cases which have a risk for hypertension, cerebral stroke, cerebral infarction, myocardial infarction, etc.

The "SGLT1 inhibiting compounds" as referred to herein may be exemplified by the following compounds:

(i) C-phenyl glucitol compounds represented by the following general formula (II) which are disclosed in International Publication WO2007/136116

[Formula 2]

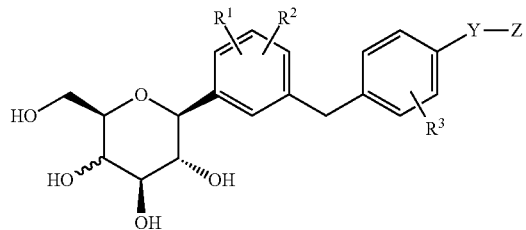

(where the definitions of substituents $R^1$, $R^2$, $R^3$, Y and Z in formula (II) are in accordance with the disclosure of International Publication WO2007/136116.)

(ii) C-phenyl 1-thioglucitol compounds represented by the following general formula (III) which are disclosed in International Publication WO2008/001864

[Formula 3]

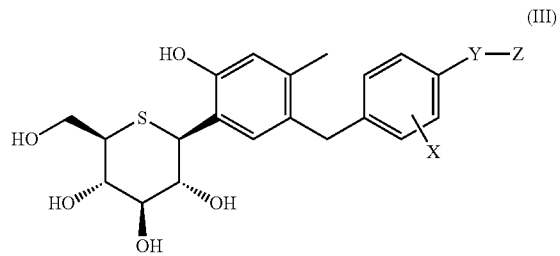

(where the definitions of substituents X, Y and Z in formula (III) are in accordance with the disclosure of International Publication WO2008/001864.)

(iii) the 1-phenyl 1-thio-D-glucitol compounds listed below which are disclosed in International Publication WO2008/072726:

(1S)-1,5-anhydro-1-[4-methyl-5-(4-methylbenzyl)-2-hydroxyphenyl]-1-thio-D-glucitol;

(1S)-1,5-anhydro-1-[5-(4-methoxybenzyl)-4-methyl-2-hydroxyphenyl]-1-thio-D-glucitol;

(1S)-1,5-anhydro-1-[5-(4-ethylbenzyl)-2-hydroxy-4-methylphenyl]-1-thio-D-glucitol;

(1S)-1,5-anhydro-1-[2-hydroxy-4-methyl-5-[4-(methylsulfanyl)benzyl]phenyl]-1-thio-D-glucitol;

(1S)-1,5-anhydro-1-[4-chloro-2-hydroxy-5-(4-methylbenzyl)phenyl]-1-thio-D-glucitol;

(1S)-1,5-anhydro-1-[4-chloro-2-hydroxy-5-(4-ethylbenzyl) phenyl]-1-thio-D-glucitol; and (1S)-1,5-anhydro-1-[4-chloro-2-hydroxy-5-(4-methoxybenzyl)phenyl]-1-thio-D-glucitol.

(iv) 4-isopropylphenyl glucitol compounds represented by the following general formula (IV) which are disclosed in International Publication WO2010/095768

[Formula 4]

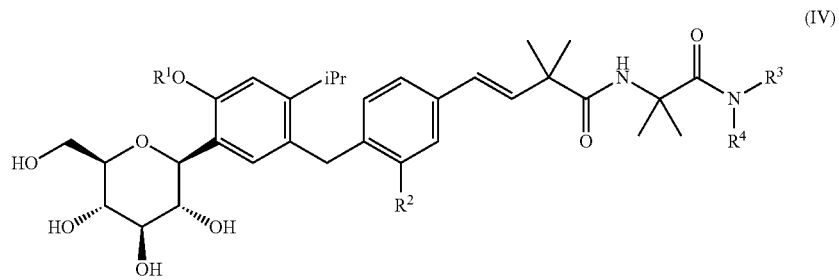

(where the definitions of substituents $R^1$, $R^2$, $R^3$ and $R^4$ in formula (IV) are in accordance with the disclosure of International Publication WO02010/095768, and specifically,
$R^1$ is a hydrogen atom or a $C_{1-4}$ alkyl group,
$R^2$ is a hydrogen atom or a methyl group,
$R^3$ is a $C_{1-4}$ alkyl group substituted by an amino group or a di-$C_{1-4}$ alkylamino group, or a piperidyl group,
$R^4$ is a hydrogen atom or $R^3$ and $R^4$, together with the adjacent nitrogen atom, form a piperidino group or a piperazinyl group, which may be substituted by a $C_{1-4}$ alkyl group or a dimethylamino group.)

The compounds represented by the foregoing general formula (IV) are more specifically exemplified by the following:

[Formula 5]

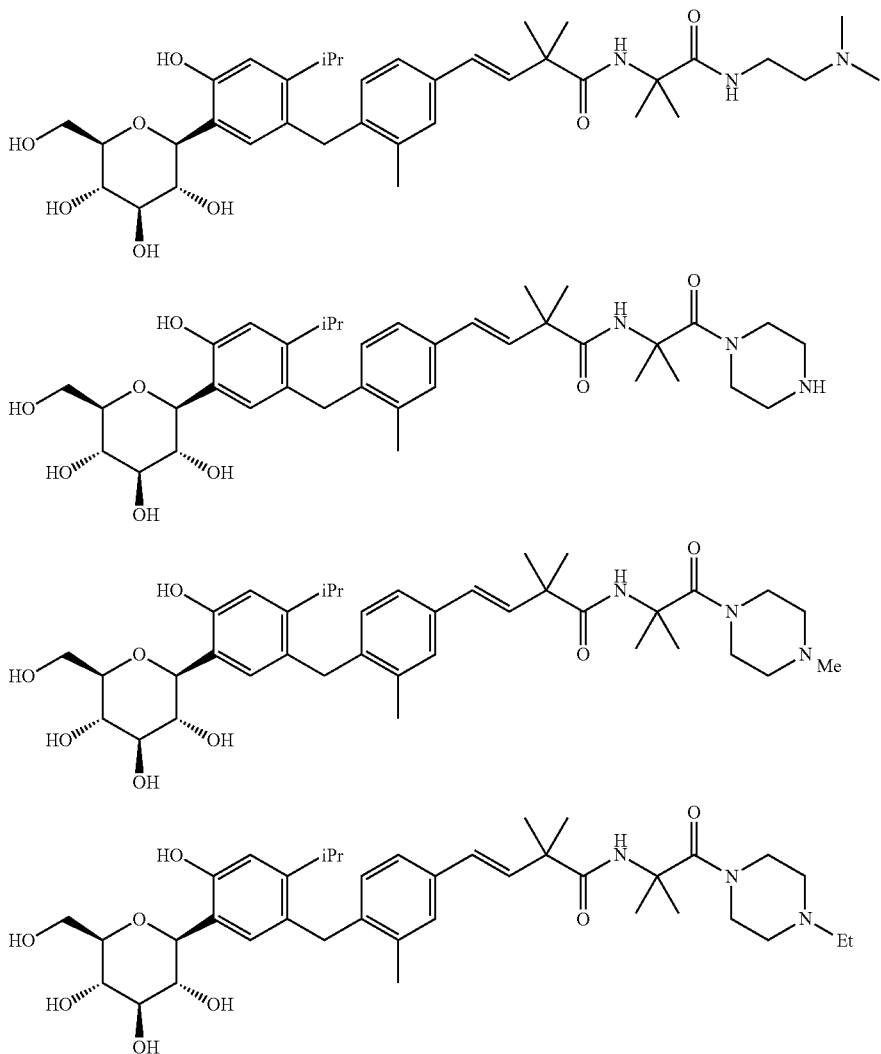

-continued
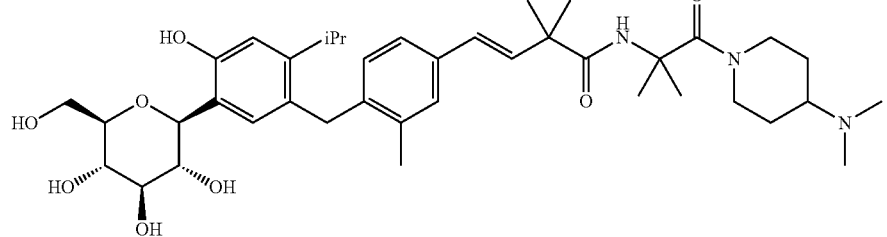
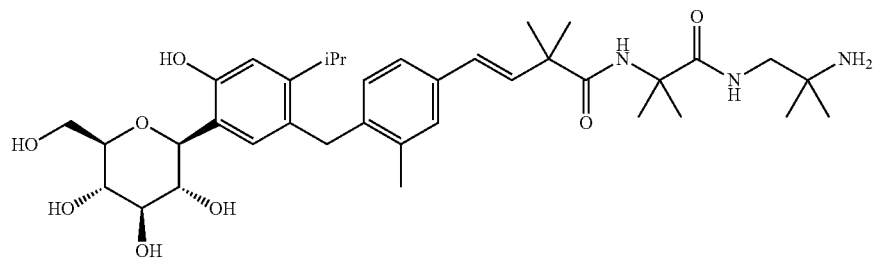
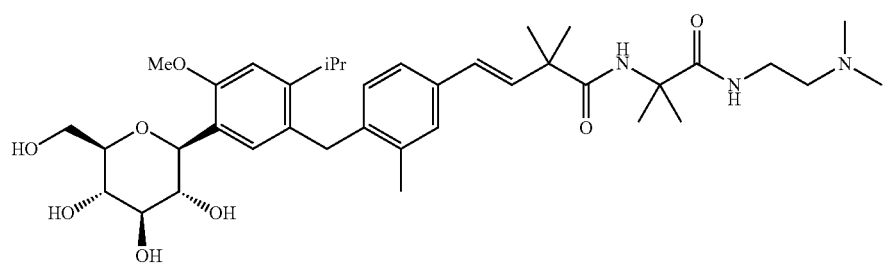
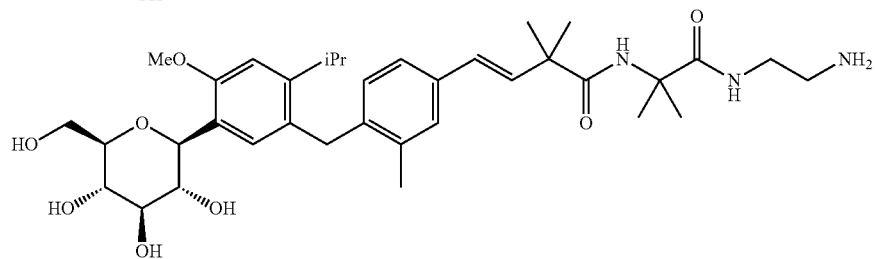
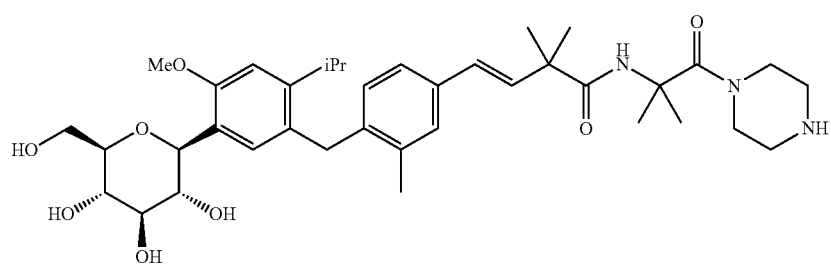
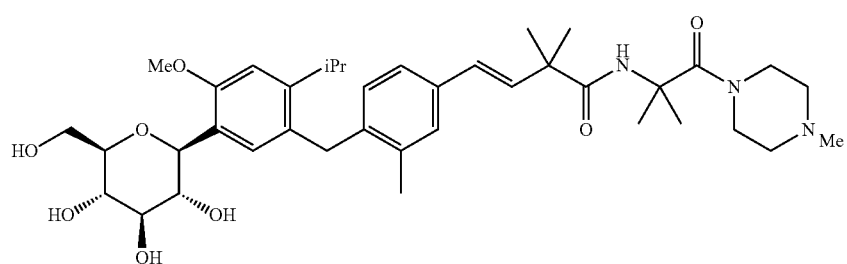

-continued
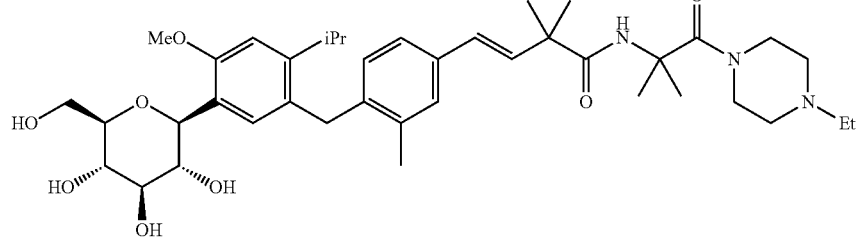
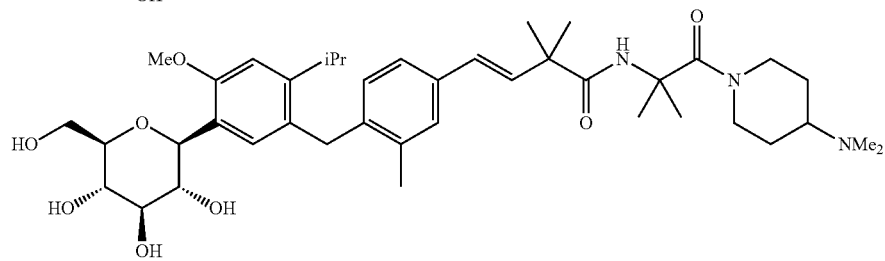
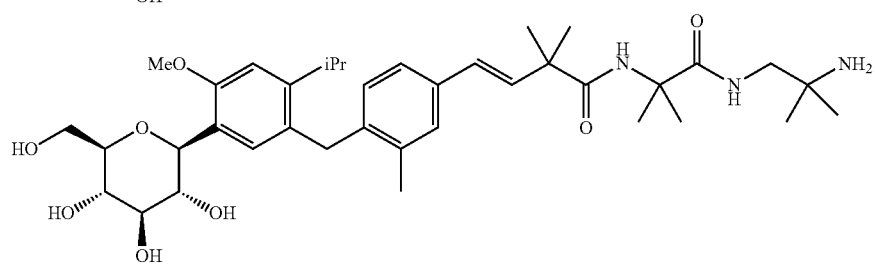
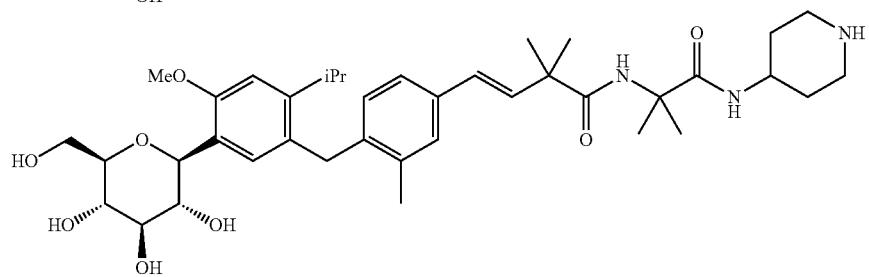
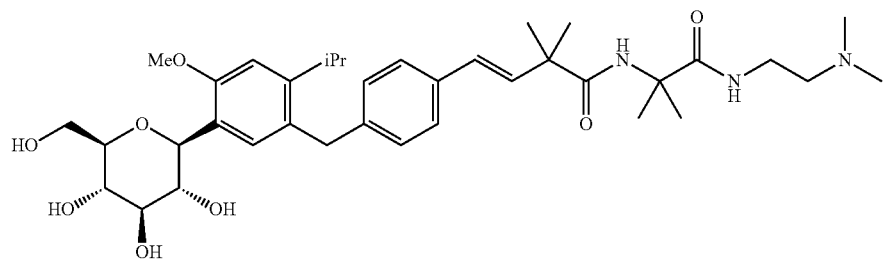
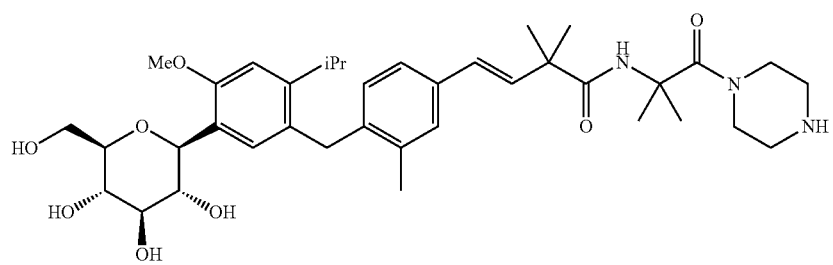

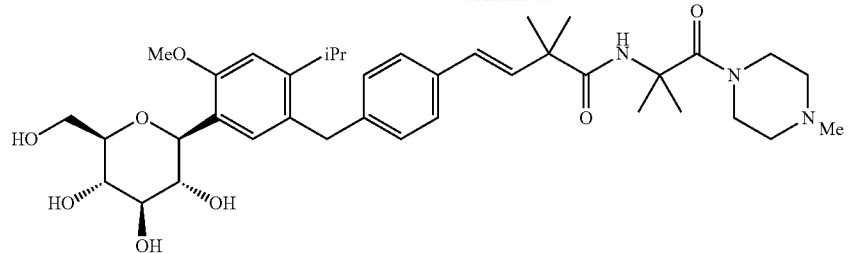

Note that the compound represented by the foregoing formula (I) is one of the compounds represented by the above general formula (IV):

[Formula 6]

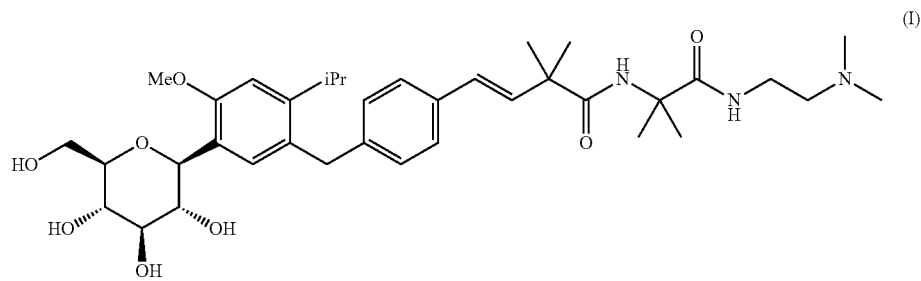

(I)

(v) (E)-N-(1-amino-2-methyl-1-oxopropan-2-yl)-4-(4-(2-isopropyl-4-methoxy-5-((2S,3R,4R,5 S,6R)-3,4,5-trihydroxy-6-(hydroxymethyl)tetrahydro-2H-pyran-2-yl)benzyl)-3-methylphenyl)-2,2-dimethylbut-3-enamide which is disclosed in International Publication WO2012/023600

[Formula 7]

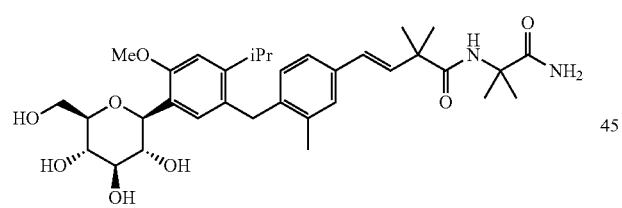

(vi) 4-isopropylphenyl glucitol compounds represented by the following general formula (V) which are disclosed in International Publication WO2012/023582

[Formula 8]

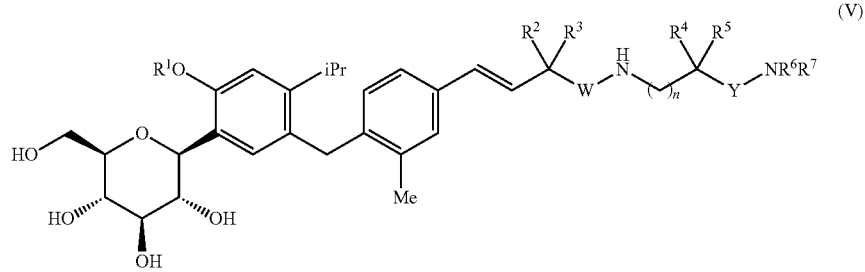

(V)

(where the definitions of substituents $R^1$, $R^2$, $R^3$, $R^4$, $R^5$, $R^6$, $R^7$, W, Y and n in formula (V) are in accordance with the disclosure of International Publication WO2012/023582.)

(vii) pyrazole compounds represented by the following general formula (VI) which are disclosed in International Publication WO2004/014932

[Formula 9]

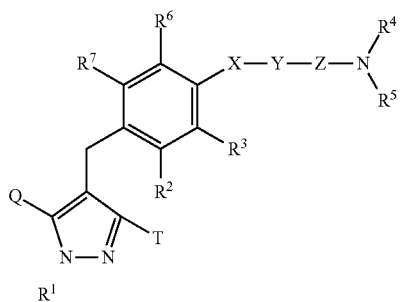

(VI)

(where the definitions of substituents $R^1$, $R^2$, $R^3$, $R^4$, $R^5$, $R^6$, $R^7$, Q, T, X, Y and Z in formula (VI) are in accordance with the disclosure of International Publication WO2004/014932.)

(viii) pyrazole compounds represented by the following general formula (VII) which are disclosed in International Publication WO2004/018491

[Formula 10]

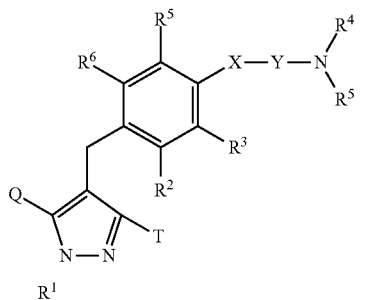

(VII)

(where the definitions of substituents $R^1$, $R^2$, $R^3$, $R^4$, $R^5$, $R^6$, Q, T, X, Y and Z in formula (VII) are in accordance with the disclosure of International Publication WO2004/018491.)

(ix) pyrazole compounds represented by the following formula (VIII) which are disclosed in International Publication WO2004/019958

[Formula 11]

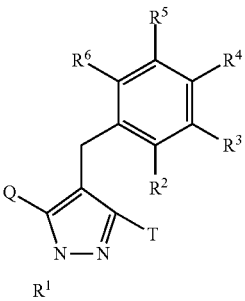

(VIII)

(where the definitions of substituents $R^1$, $R^2$, $R^3$, $R^4$, $R^5$, $R^6$, Q and T in formula (VIII) are in accordance with the disclosure of International Publication WO2004/019958.)

(x) 3-(3-{4-[3-(β-D-glucopyranosyloxy)-5-isopropyl-1H-pyrazol-4-ylmethyl]-3-methylphenoxy}propylamino)-2,2-dimethylpropionamide as disclosed in International Publication WO2009/084531 and International Publication WO2009/128421;

(xi) 5-hydroxy-3-methyl-2-{4-[3-(3-pyridylmethyl)ureido]benzyl}phenyl β-D-glucopyranoside and 3-β-D-glucopyranosyloxy)-4-{[4-(2-guanidinoethoxy)-2-methylphenyl]methyl}-5-isopropyl-1H-pyrazole which is disclosed in International Publication WO2004/050122;

(xii) benzylphenylglucopyranoside compounds represented by the following general formula (IX) which are disclosed in International Publication WO2008/016132

[Formula 12]

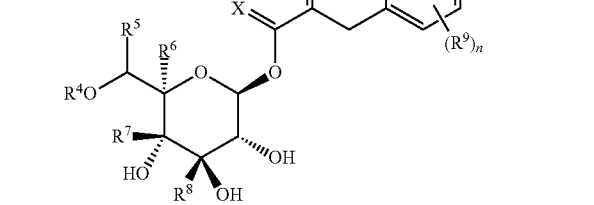

(IX)

(where the definitions of substituents $R^1$, $R^2$, $R^3$, $R^4$, $R^5$, $R^6$, $R^7$, $R^8$, $R^9$, X and n in formula (IX) are in accordance with the disclosure of International Publication WO2008/016132.)

(xiii) fluoroglucoside compounds represented by the following general formula (X) which are disclosed in International Publication WO2005/121161

[Formula 13]

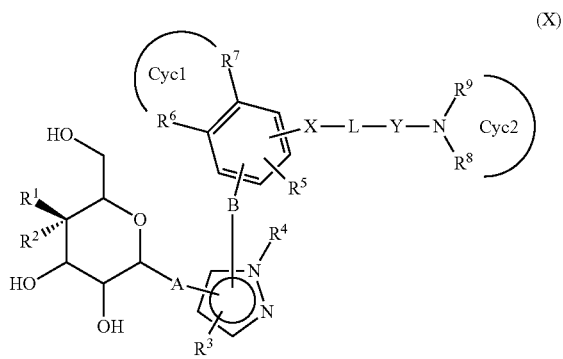

(where the definitions of substituents $R^1$, $R^2$, $R^3$, $R^4$, $R^5$, $R^6$, $R^7$, $R^8$, $R^9$, A, B, X, L, Y, Cyc1 and Cyc2 in formula (X) are in accordance with the disclosure of International Publication WO2005/121161.)

(xiv) compounds represented by the following general formula (XI) which are disclosed in International Publication WO2008/042688

[Formula 14]

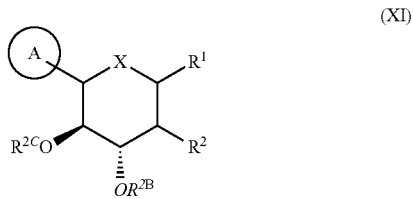

(where the definitions of substituents $R^1$, $R^2$, $R^{2B}$, $R^{2C}$, A and X in formula (XI) are in accordance with the disclosure of International Publication WO2008/042688.)

The "SGLT1 inhibiting compounds" may form pharmaceutically acceptable salts, as well as a variety of solvates including hydrates. The compound of formula (I) may take on a crystalline form, which is disclosed in WO2012/023598.

The "salts" as referred to herein are in no way limited as long as they are capable of forming pharmaceutically acceptable salts with the SGLT1 inhibiting compounds and examples include: acid addition salts including mineral acid salts such as hydrochloride, hybrobromide, hydroiodide, phosphate, sulfate and nitrate, sulfonic acid salts such as methanesulfonate, ethanesulfonate, benzenesulfonate, p-toluenesulfonate, and trifluoromethanesulfonate, and organic acid salts such as oxalate, tartrate, citrate, maleate, succinate, acetate, benzoate, mandelate, ascorbate, lactate, gluconate, malate, fumarate, and monosebacate; amino acid salts such as glycine salt, lysine salt, arginine salt, ornithine salt, glutamate, and aspartate; inorganic salts such as lithium salt, sodium salt, potassium salt, calcium salt, and magnesium salt; and salts with organic bases such as ammonium salt, triethylamine salt, diisopropylamine salt, and cyclohexylamine salt. It should be noted here that the salts include hydrous salts.

The "SGLT1 inhibiting compounds" as referred to herein may have a center of asymmetry and, in that case, a variety of optical isomers occur. Therefore, the compounds of the present invention are able to occur as separate optically active (R) and (S) forms; alternatively, they may occur as a racemate or an (RS) mixture. In the case of compounds having two or more centers of asymmetry, additional forms are also available—diastereomers due to the optical isomerism from each center of asymmetry. The compounds of the present invention even encompass those which contain all of these forms in desired proportions. The diastereomers can be separated by methods well known to the skilled artisan, for example, fractionating crystallization and the optically active forms can be obtained by techniques in organic chemistry that are well known for this purpose. In addition, the compounds of the present invention may sometimes occur as geometric isomers including a cis- and a trans-form. The compounds of the present invention encompass those isomers as well as entities containing such isomers in desired proportions.

The inhibitory activity against SGLT1 of the SGLT1 inhibiting compounds can be measured by known methods.

Hence, any person having ordinary knowledge in the technical field to which the present invention belongs can employ those known methods to assay any compound for its inhibitory activity on SGLT1 and identify compounds that are capable of inhibiting SGLT1.

Hereinafter described is a test example showing that SGLT1 inhibiting compounds according to the present invention are useful as pharmaceutical compositions for ameliorating constipation (Test 1). The compound used in the test example is the one represented by the aforementioned formula (I) ((1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol).

The compound (I) was already disclosed in Example 15-2 of International Publication WO2010/095768 and can be obtained by the method described in this document. In addition, a crystal of this compound can be obtained by the method described in International Publication WO2012/023598.

The compound (I) can also be obtained by the method to be later described in Reference Examples.

Heretofore, the compounds described under (i) to (xiv) above or pharmaceutically acceptable salts thereof are known as SGLT1 inhibiting compounds. As already mentioned above, the SGLT1 inhibiting action of these known compounds can be confirmed by known techniques.

And the compounds verified to have the SGLT1 inhibiting action or pharmaceutically acceptable salts thereof are useful as the active ingredient of the pharmaceutical compositions for ameliorating constipation according to the present invention.

The "SGLT1 inhibiting compounds" are preferably exemplified by the 4-isopropylphenyl glucitol compounds described under (iv) to (v) above or pharmaceutically acceptable salts thereof.

Particularly preferred is the following compound represented by formula (I): (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol.

The prophylactic or therapeutic drug for constipation according to the present invention can be produced by various methods, for example, the methods described in the foregoing documents.

The prophylactic or therapeutic drug for constipation according to the present invention can be administered either orally or parenterally. The preferred method of administration is by the oral route.

The prophylactic or therapeutic drug for constipation according to the present invention can be prepared from the aforementioned SGLT1 inhibiting compounds or pharmaceutically acceptable salts thereof and known carriers, diluents or other appropriate additives, which are formulated together into suitable forms of pharmaceutical composition.

Specifically, when used as oral agents, they may be tablets, dusts, powders, granules, liquids/solutions, capsules, dry syrups, jellies, etc.

The prophylactic or therapeutic drug for constipation according to the present invention can be formulated by commonly employed methods. Preferred dosage forms include tablets, powders, subtilized granules, granules, coated tablets, capsules, syrups, troches, inhalants, etc.

The prophylactic or therapeutic drugs for constipation according to the present invention, when they are to be prepared in the form of an oral agent, may be mixed with other known additives, in a qualitative and a quantitative range that will not impair the intended effects of the present invention, as exemplified by vitamins, amino acids, crude drugs, naturally occurring substances, excipients, pH modifiers, algefacients, suspending agents, viscous agents, solvent promoters, disintegrants, binders, lubricants, antioxidants, coating agents, colorants, flavoring agents, surfactants, plasticizers, perfumes, stabilizers, etc.

Exemplary excipients include lactose, starch, microcrystalline cellulose, mannitol, maltose, calcium hydrogen phosphate, light silicic anhydride, calcium carbonate, etc.; exemplary disintegrants include starch, carboxymethylcellulose calcium, etc.; exemplary binders include starch, polyvinylpyrrolidone, hydroxypropyl cellulose, ethylcellulose, carboxymethylcellulose, gum Arabic, etc.; exemplary lubricants include magnesium stearate, talc, hardened oil, etc.; and exemplary stabilizers include lactose, mannitol, maltose, polysorbates, macrogols, polyoxyethylene hardened castor oil, etc.

The dosage of the prophylactic or therapeutic drug for constipation according to the present invention is variable with the subject of administration, the route of administration, the disease to be targeted, the symptoms of the disease, etc. but in the case of oral administration to adult patients suffering from constipation, the usual single dose ranges from 0.1 mg to 1000 mg, preferably from 1 mg to 200 mg in terms of the active ingredient; this amount is desirably dosed once to three times a day, preferably before or after meal.

According to the present invention, there can be provided novel drugs for constipation that are effective in ameliorating constipation. The prophylactic or therapeutic drugs for constipation according to the present invention are useful as pharmaceuticals that prevent or treat constipation or as pharmaceuticals that promote defecation. In addition, the SGLT1 inhibiting compounds according to the present invention or pharmaceutically acceptable salts thereof show superior inhibitory action on SGLT1 and they are useful as pharmaceuticals that prevent or treat constipation or as pharmaceuticals that promote defecation. Therefore, the pharmaceutical compositions according to the present invention and the SGLT1 inhibiting compounds according to the present invention are useful as prophylactic or therapeutic drugs for various kinds of constipation and effective as prophylactic or therapeutic drugs for various kinds of constipation that are manifested either acutely or chronically, for example, functional constipation, organic constipation, symptomatic constipation, drug-induced constipation, etc. as well as constipation in irritable bowel syndrome, constipation that accompanies physiological changes in the elderly on account of the aging intestinal tract, constipation in women due, for example, to hormonal actions during the menstruation cycle, constipation in pregnant women, and constipation as a somatic symptom of a mental disease such as depression or anxiety neurosis. In addition, the use of the pharmaceutical compositions according to the present invention and the SGLT1 inhibiting compounds according to the present invention is not limited to the prevention or treatment of the various types of constipation mentioned above and they may also be used as defecation promoting pharmaceuticals for various purposes, e.g. emptying the intestinal tract during digestive tract examination or both before and after abdominal surgery, assisting in defecation after surgery, or promoting defecation after dosing of a contrast medium. Utility also exists as medicaments for emptying the digestive tract of harmful materials such as undigested materials or toxic substances. Further utility also exists as medicaments for promoting defecation in those cases which have a risk for hypertension, cerebral stroke, cerebral infarction, myocardial infarction, etc.

Hereinafter are given reference examples, test examples, and formulation examples to describe the present invention more specifically but it should be understood that the present invention will by no means be limited by these examples.

By the following reference examples, a method for synthesizing the compound (I) is shown.

Compound (I) can be produced in accordance with Scheme 1 outlined below.

Scheme 1: Production of compound (I)

[Formula 15]

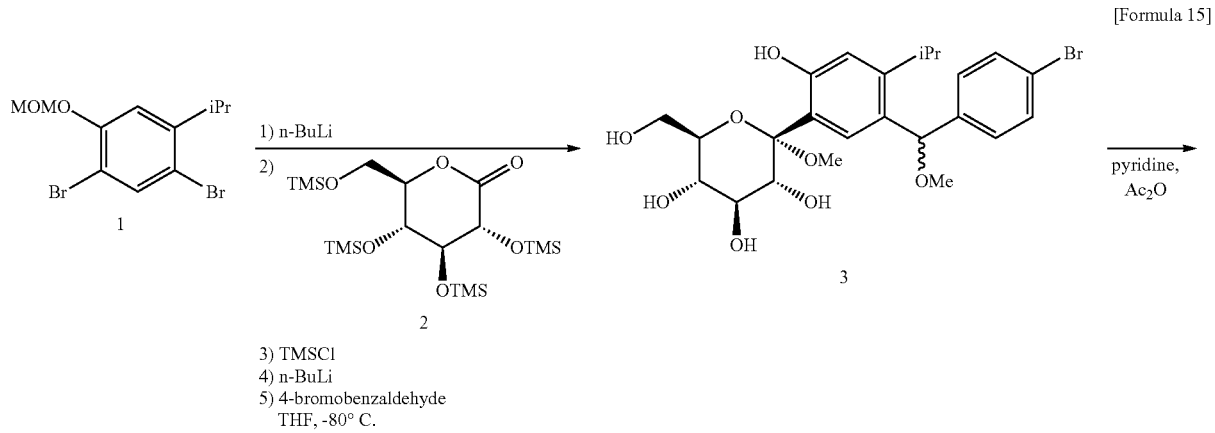

-continued
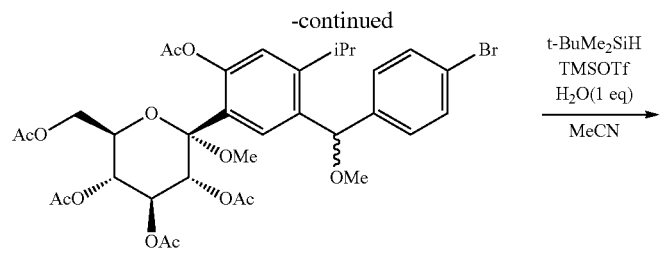
4
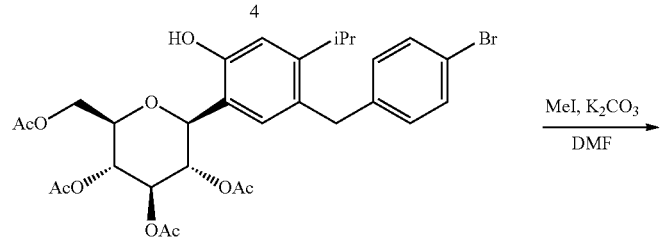
5
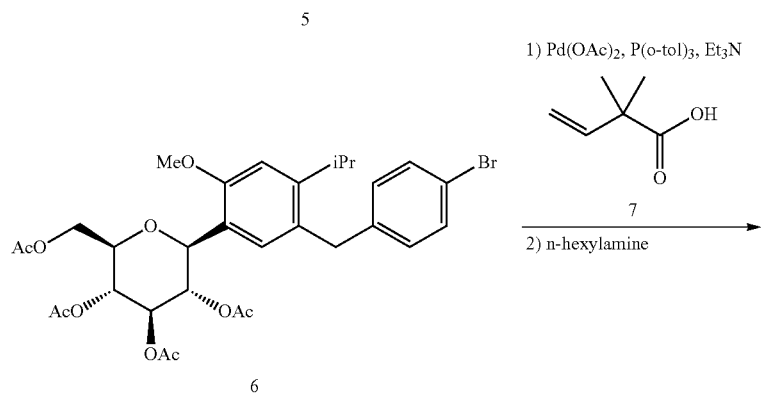
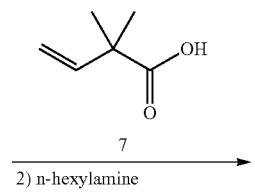
6
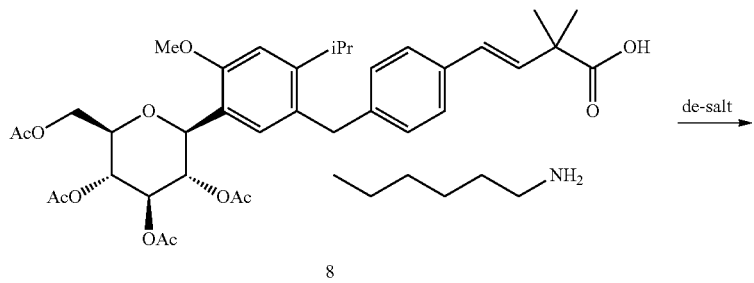
8
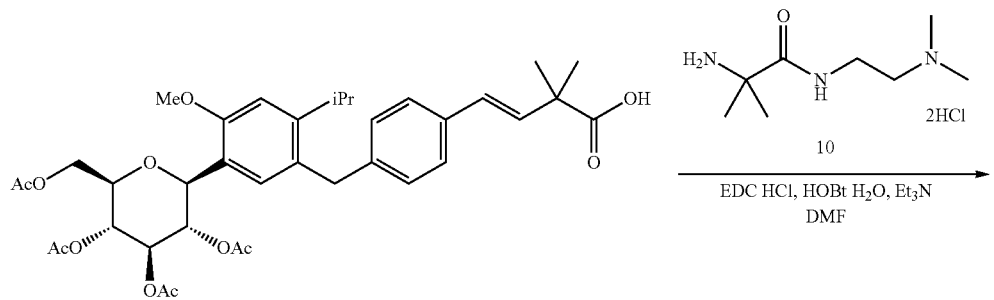
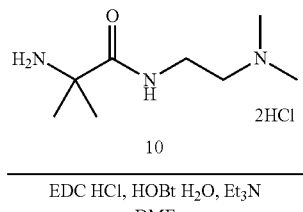
9

-continued

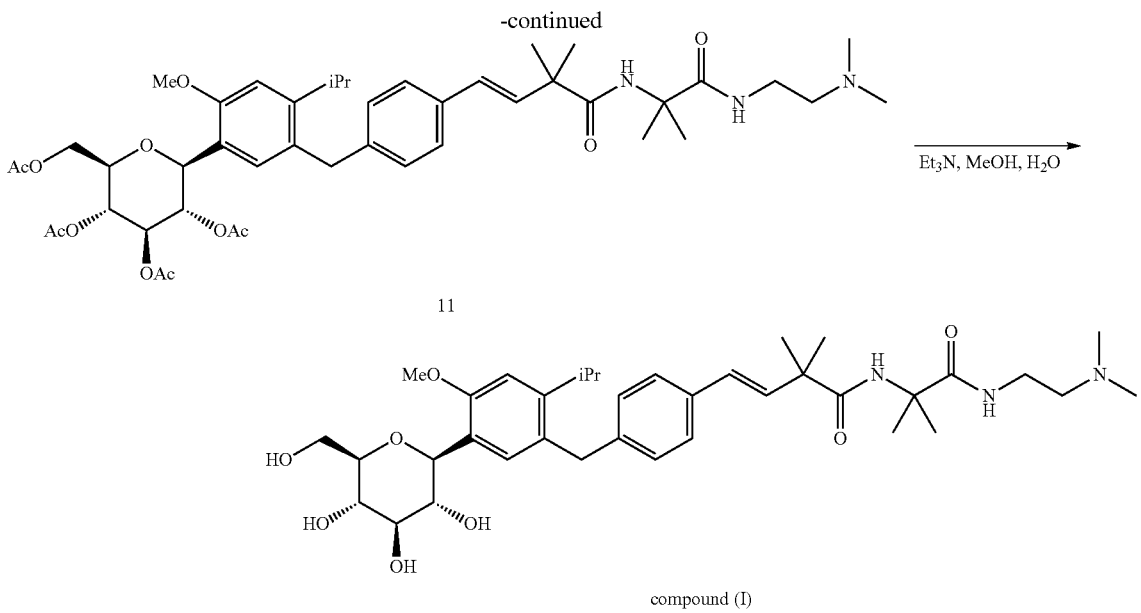

(In the scheme, MOM stands for methoxymethyl and TMS, trimethylsilyl.)

REFERENCE EXAMPLE 1

Production of Compound (I)
Step 1: Production of Compound 3

To a solution of compound 1 (95.0 g, 281 mmol) in tetrahydrofuran (1395 mL), n-butyllithium hexane solution (2.66 M, 111 mL) was added dropwise in an argon atmosphere at −75 to −72° C. over 45 minutes, followed by stirring at −75 to −72° C. for 33 minutes. Subsequently, a solution of compound 2 (138 g, 295 mmol) in tetrahydrofuran (400 mL) was added dropwise at −78 to −73° C. over one hour and 37 minutes, followed by stirring at −76 to −73° C. for 20 minutes. Subsequently, trimethylsilyl chloride (32.1 g, 295 mmol) was added dropwise at −76 to −73° C. over 5 minutes, followed by stirring at −76 to −73° C. for one hour and 15 minutes. Subsequently, n-butyllithium hexane solution (2.66 M, 153 mL) was added at −76 to −72° C. over one hour and 5 minutes, followed by stirring at −76 to −72° C. for 20 minutes. Subsequently, a solution of 4-bromobenzaldehyde (57.2 g, 309 mmol) in tetrahydrofuran (400 mL) was added at −75 to −72° C. over one hour and 5 minutes, followed by stirring at −75 to −72° C. for 20 minutes. To the reaction mixture, water (1430 mL) and toluene (1430 mL) were added for separation into the organic and the aqueous layer. After distilling off the organic layer under reduced pressure, the residue was dissolved in methanol (1378 mL) and to the resulting solution, methanesulfonic acid (2.70 g, 28.1 mmol) was added and the mixture was heated under reflux for an hour. After cooling to 25° C., triethylamine (5.69 g, 56.2 mmol) was added. After subsequent distilling off under reduced pressure, the residue was dissolved in toluene (634 mL) and the resulting solution was washed with water three times for separation into the organic and the aqueous layer. To the organic layer, 1 M aqueous sodium hydroxide solution (350 mL) and toluene (550 mL) were added and the mixture was stirred, followed by separation into the organic and the aqueous layer. To the aqueous layer, toluene (250 mL) was added and the mixture was stirred, followed by separation into the organic and the aqueous layer. To the aqueous layer, 1 M hydrochloric acid (400 mL) and toluene (550 mL) were added and the mixture was stirred, followed by separation into the organic and the aqueous layer. The organic layer was washed with 10% aqueous sodium chloride solution (550 mL), followed by separation into the organic and the aqueous layer. The organic layer was distilled off under reduced pressure and the resulting crude product (111 g) was subjected to silica gel column chromatography [successively eluted with chloroform:methanol=20:1, 10:1, and 5:1 (v/v)] and the fractions of the higher purity were concentrated to give compound 3 (1.10 g) as a pale yellow amorphous.

$^1$H NMR (500 MHz, DMSO-$d_6$) with the reference TMS (0.00 ppm)

δ: 0.93 (1.65H, d, J=6.6 Hz), 0.94 (1.35H, d, J=6.6 Hz), 0.97 (3H, d, J=6.6 Hz), 2.99 (1.65H, s), 3.04 (1.35H, s), 3.05 (1H, septet, J=6.6 Hz), 3.15 (1H, dd, J=8.9 and 4.0 Hz), 3.25 (1.35H, s), 3.26 (1.65H, s), 3.29-3.38 (1H, m), 3.41-3.47 (1H, m), 3.57-3.60 (1H, m), 3.65-3.72 (2H, m), 4.70-4.78 (1H, m, exchangeable with $D_2O$), 4.87 (0.55H, d, J=5.5 Hz, exchangeable with $D_2O$), 4.88 (0.45H, d, J=5.8 Hz, exchangeable with $D_2O$), 5.03 (0.55H, d, J=5.5 Hz, exchangeable with $D_2O$), 5.04 (0.45H, d, J=5.5 Hz, exchangeable with $D_2O$), 5.44 (1H, s), 5.63 (1H, br s, exchangeable with $D_2O$), 6.66 (0.45H, s), 6.67 (0.55H, s), 7.15-7.24 (2H, m), 7.32 (0.55H, s), 7.38 (0.45H, s), 7.46-7.53 (2H, m), 8.80 (0.55H, s, exchangeable with $D_2O$), 8.82 (0.45H, s, exchangeable with $D_2O$).

$^{13}$C NMR (125 MHz, DMSO-$d_6$) with the reference DMSO-$d_6$ (39.5 ppm)

δ: 23.4, 23.5, 23.7, 27.46, 27.54, 48.5, 48.6, 56.20, 56.22, 59.7, 59.8, 69.26, 69.32, 73.8, 76.2, 81.1, 102.2, 102.3, 114.3, 114.4, 120.0, 120.1, 120.5, 127.5, 127.6, 129.0, 129.1, 129.3, 130.87, 130.90, 141.9, 142.1, 148.3, 148.4, 154.8.

MS ESI/APCI dual posi, m/z: 551 [(M+2)+Na]$^+$, 549 (M+Na)$^+$.

MS ESI/APCI dual nega, m/z: 527 [(M+2)−H]$^-$, 525 (M−H)$^-$.

REFERENCE EXAMPLE 2

Step 2: Production of Compound 4

To a solution of compound 3 (8.92 g) in pyridine (30.0 mL), acetic anhydride (12.8 mL) was added, followed by stirring at 22 to 27° C. for 23 hours and 40 minutes. The reaction mixture was cooled on an ice water bath and after adding water (30.0 mL), the mixture was stirred for 10 minutes and then toluene (50.0 mL) was added. After separation into the organic and the aqueous layer, the aqueous layer was extracted with toluene (50.0 mL), followed by separation into the organic and the aqueous layer. The combined organic layers were washed with 2 M hydrochloric acid (50.0 mL) three times and then washed successively with saturated aqueous sodium hydrogencarbonate solution (50.0 mL) and saturated aqueous sodium chloride solution (50.0 mL), followed by separation into the organic and the aqueous layer. The organic layer was dried over anhydrous magnesium sulfate (7.02 g) and, thereafter, the solvent was distilled off under reduced pressure, then dried under reduced pressure to yield a crude product (12.1 g). The crude product was subjected to silica gel column chromatography [eluted with hexane:ethyl acetate=2:1 (v/v)] to give compound 4 (1.10 g) as a colorless amorphous.

$^1$H NMR (500 MHz, CDCl$_3$) with the reference TMS (0.00 ppm)

δ: 1.06 (1.95H, d, J=6.9 Hz), 1.10 (1.05H, d, J=6.7 Hz), 1.15 (1.05H, d, J=6.7 Hz), 1.18 (1.95H, d, J=6.9 Hz), 1.55 (1.05H, s), 1.92 (1.95H, s), 1.96 (1.05H, s), 1.98 (1.95H, s), 2.05 (3H, s), 2.06 (1.95H, s), 2.07 (1.05H, s), 2.34 (1.95H, s), 2.35 (1.05H, s), 3.04-3.13 (0.35H, m), 3.08 (1.95H, s), 3.17 (0.65H, septet, J=6.9 Hz), 3.27 (1.05H, s), 3.30 (1.95H, s), 3.37 (1.05H, s), 3.98-4.09 (2H, m), 4.36-4.46 (1H, m), 5.13-5.21 (1H, m), 5.25-5.33 (1H, m), 5.44 (0.65H, s), 5.46 (0.35H, s), 5.54 (0.35H, t, J=9.6 Hz), 5.56 (0.65H, t, J=9.6 Hz), 6.92 (0.65H, s), 6.95 (0.35H, s), 7.03-7.08 (0.7H, apparent d as part of AA'XX' system, J=8.2 Hz), 7.12-7.16 (1.3H, apparent d as part of AA'XX' system, J=8.5 Hz), 7.38 (0.65H, s), 7.39-7.43 (0.7H, apparent d as part of AA'XX-'system, J=8.8 Hz), 7.42 (0.35H, s), 7.43-7.46 (1.3H, apparent d as part of AA'XX' system, J=8.2 Hz).

$^{13}$C NMR (125 MHz, CDCl$_3$) with the reference CDCl$_3$ (77.0 ppm)

δ: 20.1, 20.4, 20.59, 20.62, 20.7, 21.3, 21.4, 22.9, 23.5, 23.8, 24.3, 28.5, 49.7, 49.8, 56.8, 57.1, 62.4, 68.69, 68.72, 68.78, 68.81, 71.4, 71.5, 72.5, 72.6, 80.4, 101.2, 121.37, 121.43, 122.1, 122.4, 124.5, 124.8, 128.5, 128.6, 128.7, 129.4, 131.4, 134.7, 135.2, 140.7, 140.8, 148.5, 148.6, 149.61, 149.64, 168.9, 169.0, 169.20, 169.24, 169.7, 170.0, 170.1, 170.5.

MS ESI/APCI dual posi, m/z: 761 [(M+2)+Na]$^+$, 759 (M+Na)+, 756 [(M+2)+NH$_4$]$^+$, 754 (M+NH$_4$)$^+$.

REFERENCE EXAMPLE 3

Step 3: Production of Compound 5

To a solution of compound 4 (9.62 g) in acetonitrile (96.0 mL), tert-buthyldimethyl silane (6.07 g) and water (0.235 mL) were added and the mixture was cooled on an ice water bath. To the cooled mixture, trimethylsilyl trifluoromethanesulfonate (10.1 mL) was added at 1 to 7° C. over 13 minutes, followed by stirring at 5 to 11° C. for one hour and 15 minutes. To the reaction mixture, toluene (100 mL) was added and the resulting mixture was washed with 3% aqueous sodium hydrogencarbonate solution (50.0 mL) twice. After distilling off the organic layer under reduced pressure, the residue was dried under reduced pressure to yield a colorless amorphous crude product (9.29 g). The crude product was subjected to silica gel column chromatography [eluted successively with hexane:ethyl acetate=2:1 and 1:1 (v/v) and ethyl acetate] to give compound 5 (1.12 g) as a colorless powder.

$^1$H NMR (500 MHz, DMSO-d$_6$) with the reference TMS (0.00 ppm)

δ: 0.92 (3H, d, J=6.7 Hz), 1.02 (3H, d, J=6.7 Hz), 1.73 (3H, s), 1.93 (3H, s), 1.99 (3H, s), 2.01 (3H, s), 2.90 (1H, septet, J=6.7 Hz), 3.83, 3.90 (2H, AB quartet, J=15.9 Hz), 4.00-4.11 (3H, m), 4.91 (1H, d, J=9.7 Hz), 5.04 (1H, t, J=9.7 Hz), 5.26 (1H, t, J=9.7 Hz), 5.34 (1H, t, J=9.7 Hz), 6.72 (1H, s), 6.97-7.03 (2H, apparent d as part of AA'XX' system, J=8.4 Hz), 7.05 (1H, s), 7.38-7.43 (2H, apparent d as part of AA'XX' system, J=8.4 Hz), 9.34 (1H, s, exchangeable with D$_2$O).

$^{13}$C NMR (125 MHz, DMSO-d$_6$) with the reference DMSO-d$_6$ (39.5 ppm)

δ: 20.1, 20.3, 20.4, 20.5, 23.3, 23.8, 28.4, 36.8, 62.4, 68.5, 71.5, 72.8, 73.8, 74.6, 112.4, 118.6, 119.8, 126.9, 130.3, 130.6, 130.9, 141.3, 148.1, 154.5, 168.6, 169.4, 169.6, 170.1

MS ESI/APCI dual posi, m/z: 659 [(M+2)+Na]$^+$, 657 (M+Na)$^+$.

MS (ESI/APCI dual nega, m/z: 635 [(M+2)–H]$^-$, 633 (M–H)$^-$.

REFERENCE EXAMPLE 4

Step 4: Production of Compound 6

To a solution of compound 5 (170 g, 0.268 mol) in N,N-dimethylformamide (85 mL), potassium carbonate (111 g, 0.804 mol) was added and methyl iodide (50.1 mL, 0.804 mol) was added over 6 minutes. The reaction mixture was stirred at room temperature for 6 hours and 30 minutes, followed by addition of toluene (852 mL) and water (1.7 L). The organic layer was separated and after being washed with water (853 mL) twice, washed with 10% aqueous sodium chloride solution (426 mL); after the organic layer was dried over anhydrous magnesium sulfate, the solvent was distilled off under reduced pressure to yield a crude product (203 g). The resulting residue was subjected to silica gel chromatography [hexane:ethyl acetate=3:2 (v/v)] to give a pale brown amorphous (170 g). The amorphous was dissolved in isopropanol (1020 mL) and stirred overnight; the resulting crystal was recovered by filtration and dried to give compound 6 (108 g) as a colorless powder.

$^1$H NMR (300 MHz, CDCl$_3$) with the reference TMS (0.00 ppm)

δ: 1.04 (3H, d, J=6.8 Hz), 1.09 (3H, d, J=6.8 Hz), 1.76 (3H, s), 2.01 (3H, s), 2.05 (3H, s), 2.06 (3H, s), 2.91-3.06 (1H, m), 3.80-3.88 (4H, m), 3.91 (2H, d, J=5.1 Hz), 4.06-4.18 (1H, m), 4.20-4.31 (1H, m), 4.82-4.93 (1H, m), 5.15-5.43 (3H, m), 6.77 (1H, s), 6.92 (2H, d, J=8.6 Hz), 7.11 (1H, s), 7.36 (2H, d, J=8.6 Hz).

MS ESI/APCI dual posi, m/z: 671 [M+Na]$^+$, 666[M+NH$_4$]$^+$

REFERENCE EXAMPLE 5

Step 5: Production of Compound 8

To a solution of compound 6 (27.7 g, 42.7 mmol) in acetonitrile (83.0 mL), tri-o-tolylphosphine (2.60 g, 8.54 mmol), compound 7 (7.31 g, 64.0 mmol), triethylamine (23.7 mL, 171 mmol) and palladium acetate (0.958 g, 4.27 mmol) were added and the mixture was heated under reflux at 80 to 82° C. for 4 hours in an argon atmosphere. The reaction mixture was allowed to cool to 27° C. and after adding chloroform (54.0 mL) to it, the mixture was filtered through a Celite (registered trademark) pad (11.9 g) and then washed with chloroform (84.0 mL). The filtrate and the washings were distilled off under reduced pressure and to the resulting residue (56.5 g), ethyl acetate (150 mL) was added and the mixture was successively washed with 2.0 M hydrochloric acid (100 mL) and then with saturated aqueous sodium chloride solution (100 mL). The organic layer was dried over anhydrous magnesium sulfate (10.1 g) and after distilling off the solvent under reduced pressure, the residue was dried under reduced pressure to give a crude product (35.1 g) as a pale yellow amorphous.

The crude product was dissolved in ethyl acetate (130 mL) and to the resulting solution, hexylamine (4.53 g, 44.8 mmol) was added and the mixture was heated with stirring on an oil bath, followed by addition of hexane (195 mL) at 55° C. After removing the oil bath, compound 8 (0.004 g) was added as a seed crystal at 41° C. and the mixture was stirred at 21 to 41° C. for 4 hours and 47 minutes. The precipitating solid matter was filtered under suction and then washed with a hexane-ethyl acetate [3:2 (v/v)] liquid mixture (150 mL) that had been cooled on an ice water bath. The resulting wet solid matter was dried under reduced pressure to give compound 8 (26.7 g) as a colorless solid.

$^1$H NMR (500 MHz, CDCl$_3$) with the reference TMS (0.00 ppm)

δ: 0.82 (3H, t, J=7.3 Hz), 1.02 (3H, d, J=6.9 Hz), 1.07 (3H, d, J=6.9 Hz), 1.09-1.16 (4H, m), 1.16-1.24 (2H, m), 1.27 (6H, s), 1.43-1.54 (2H, m), 1.76 (3H, s), 2.00 (3H, s), 2.047 (3H, s), 2.052 (3H, s), 2.59-2.66 (2H, m), 3.01 (1H, septet, J=6.9 Hz), 3.80-3.85 (1H, m), 3.84 (3H, s), 3.91, 3.93 (2H, AB quartet, J=16.1 Hz), 4.13 (1H, dd, J=12.3 and 2.1 Hz), 4.25 (1H, dd, J=12.3 and 4.6 Hz), 4.85 (1H, d, J=9.5 Hz), 5.22 (1H, t, J=9.5 Hz), 5.33 (1H, t, J=9.5 Hz), 5.41 (1H, t, J=9.5 Hz), 6.29 (1H, d, J$_{AB}$=16.3 Hz), 6.44 (1H, d, J$_{AB}$=16.3 Hz), 6.50 (3H, br s, exchangeable with D$_2$O), 6.76 (1H, s), 6.92-6.97 (2H, apparent d as part of AA'XX' system, J=8.0 Hz), 7.12 (1H, s), 7.20-7.25 (2H, apparent d as part of AA'XX' system, J=8.0 Hz).

$^{13}$C NMR (125 MHz, CDCl$_3$) with the reference CDCl$_3$ (77.0 ppm)

δ: 13.9, 20.4, 20.65, 20.68, 20.8, 22.4, 23.5, 23.7, 25.9, 26.2, 28.6, 29.3, 31.2, 38.1, 39.8, 45.5, 55.7, 62.4, 68.8, 71.6, 74.4, 74.7, 76.1, 108.4, 121.3, 125.7, 126.0, 128.4, 129.5, 130.8, 135.2, 136.8, 140.2, 149.4, 156.6, 169.0, 169.6, 170.4, 170.8, 183.1.

MS ESI/APCI dual posi, m/z: 784 (M+H)$^+$, 705 [(M−C$_6$H$_{15}$N)+Na]$^+$.

MS ESI/APCI dual nega, m/z: 681 [(M−C$_6$H$_{15}$N)−H]$^−$.

REFERENCE EXAMPLE 6

Step 6: Production of Compound 9

To a solution of compound 8 (110 g) in ethyl acetate (555 mL), 1 M hydrochloric acid (222 mL) was added and the mixture was stirred. The organic layer was separated, washed with 10% aqueous sodium chloride solution (222 mL), and dried over anhydrous magnesium sulfate; thereafter, the solvent was distilled off under reduced pressure to give compound 9 (105 g) as a colorless amorphous.

$^1$H NMR (300 MHz, CDCl$_3$) with the reference TMS (0.00 ppm)

δ: 1.03 (3H, d, J=6.8 Hz), 1.09 (3H, d, J=6.8 Hz), 1.76 (3H, s), 2.00 (3H, s), 2.05 (3H, s), 2.06 (3H, s), 2.95-3.10 (1H, m), 3.79-3.83 (1H, m), 3.84 (3H, s), 3.87-4.01 (2H, m), 4.07-4.18 (2H, m), 4.20-4.29 (1H, m), 4.86 (1H, d, J=9.5 Hz), 5.22 (1H, t, J=9.3 Hz), 5.29-5.45 (2H, m), 6.30-6.38 (1H, m), 6.40-6.48 (1H, m), 6.77 (1H, s) 6.98 (2H, d, J=8.2 Hz), 7.12 (1H, s), 7.22-7.29 (2H, m).

REFERENCE EXAMPLE 7

Step 7: Production of Compound 11

To a solution of compound 9 (104.6 g, 0.104 mol) and compound 10 (46.4 g, 0.182 mol) in N,N-dimethylformamide (1050 mL), 1-hydroxybenzotriazole monohydrate (HOBt.H$_2$O) (32.2 g, 0.210 mol) and N-ethyl-N'-3-dimethylaminopropylcarbodiimide hydrochloride (EDC.HCl) (40.3 g, 0.210 mol) were added and the mixture was stirred overnight at room temperature. To the reaction mixture, water (520 mL) was added and two extractions were conducted with toluene (1050 mL). The combined organic layers were washed with 5% aqueous sodium chloride solution (520 mL) three times and dried over anhydrous magnesium sulfate; the solvent was distilled off under reduced pressure to give compound 11 (126.9 g) as a colorless amorphous.

$^1$H NMR (300 MHz, CDCl$_3$) with the reference TMS (0.00 ppm)

δ: 1.05 (3H, d, J=6.8 Hz), 1.10 (3H, d, J=6.8 Hz), 1.38 (6H, s), 1.49 (6H, s), 1.77 (3H, s), 2.00 (3H, s), 2.05 (3H, s), 2.06 (3H, s), 2.21 (6H, s), 3.04 (1H, quin, J=6.8 Hz), 3.38-3.49 (2H, m), 3.78-3.83 (1H, m), 3.85 (3H, s), 3.87-4.04 (2H, m), 4.08-4.18 (1H, m), 4.18-4.30 (1H, m), 4.87 (1H, d, J=9.5 Hz), 5.16-5.27 (1H, m), 5.28-5.44 (2H, m), 6.30 (1H, d, J=16.2 Hz), 6.51 (1H, d, J=16.2 Hz), 6.77 (1H, s), 7.01 (2H, d, J=8.2 Hz), 7.13 (1H, s), 7.32 (2H, d, J=8.2 Hz).

REFERENCE EXAMPLE 8

Step 8: Production of Compound (I)

To compound 11 (103 mg), a mixture of triethylamine/water/methanol (1/1/5, 2.5 mL) was added. The reaction mixture was stirred at room temperature for 17 hours and the solvent was distilled off under reduced pressure. The resulting residue was subjected to silica gel chromatography [chloroform and chloroform:methanol=δ: 2 (v/v)] to give compound (I) (62.1 mg) as a colorless amorphous.

$^1$H NMR (600 MHz, MeOH-d$_4$) with the reference TMS (0.00 ppm)

δ: 1.07 (3H, d, J=6.8 Hz), 1.09 (3H, d, J=6.8 Hz), 1.36 (6H, s), 1.44 (6H, s), 2.23 (6H, s), 2.41 (2H, t, J=6.9 Hz), 3.10 (1H, septet, J=6.8 Hz), 3.26-3.30 (2H, m), 3.38-4.00 (2H, m), 3.45-3.52 (1H, m), 3.54-3.60 (1H, m), 3.62-3.69 (1H, m), 3.79-3.89 (4H, m), 3.99 (2H, s), 4.65 (1H, d, J=9.6 Hz), 6.39 (1H, d, J=16.5 Hz), 6.52 (1H, d, J=16.5 Hz), 6.88 (1H, s), 7.06-7.08 (2H, m), 7.23 (1H, s), 7.30-7.32 (2H, m).

MS ESI/APCI dual posi, m/z: 670[M+H]$^+$.

MS ESI/APCI dual nega, m/z: 704[M+Cl]$^−$.

Anal. Calcd for C$_{37}$H$_{55}$N$_3$O$_8$.1.0H$_2$O: C, 64.60; H, 8.36; N, 6.11. Found: C, 64.50; H, 8.31; N, 6.02.

Note that compound 10 used in Reference Example 7 above can be produced in accordance with the following Scheme 2.

Scheme 2: Production of Compound 10

[Formula 16]

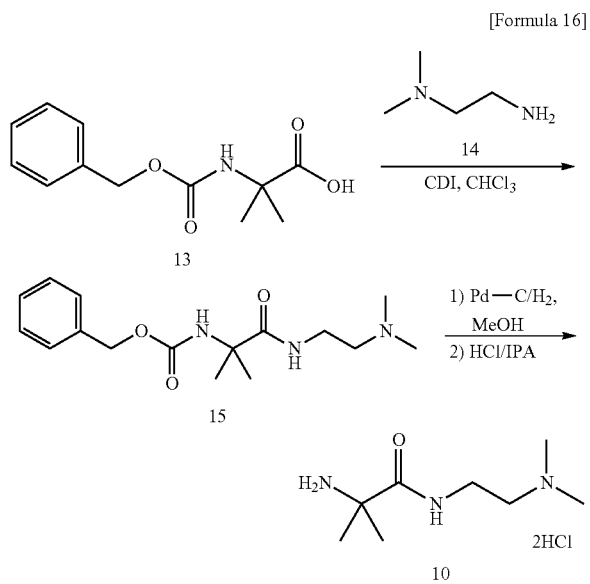

REFERENCE EXAMPLE 9

Step 1: Production of Compound 15

To a solution of compound 13 (500 mg, 2.11 mmol) in chloroform (5.0 mL), 1,1'-carbonyldiimidazole (CDI) (513 mg, 3.16 mmol) was added and the mixture was stirred at room temperature for 45 minutes. To the reaction mixture, N,N-dimethylethylenediamine (compound 14) (279 mg, 3.16 mmol) was added and the mixture was stirred at room temperature for an hour. To the reaction mixture, water (25 mL) was added and the mixture was extracted with chloroform four times. The combined organic layers were washed with 5% aqueous sodium chloride solution and thereafter dried over anhydrous magnesium sulfate; the solvent was concentrated under reduced pressure to give compound 15 (815 mg).

$^1$H NMR (300 MHz, CDCl$_3$) with the reference TMS (0.00 ppm)

δ: 1.53 (6H, s), 2.20 (6H, s), 2.31-2.43 (2H, m), 3.25-3.35 (2H, m), 5.08 (1H, s), 5.49 (1H, brs), 6.69 (1H, brs), 7.30-7.39 (5H, m).

MS ESI/APCI dual posi, m/z: 308[M+H]$^+$.
MS ESI/APCI dual nega, m/z: 342[M+Cl]$^-$.

REFERENCE EXAMPLE 10

Step 2: Production of Compound 10

To a solution of compound 15 (7.1 g) in methanol (50 mL), 10% palladium carbon (355 mg) was added and the mixture was stirred at room temperature for 2 hours in a hydrogen atmosphere. The reaction mixture was filtered through a Celite (registered trademark) pad and the filtrate was concentrated. The resulting residue (5.0 g) was dissolved in isopropanol (40 mL) and after adding conc. hydrochloric acid (6.0 mL), the mixture was stirred for 20 minutes at room temperature and for an additional 2 hours and 30 minutes under cooling with ice. The resulting solid matter was recovered by filtration and dried under heating to give compound 10 (3.0 g) as a colorless powder.

$^1$H NMR (300 MHz, DMSO-d$_6$) with the reference TMS (0.00 ppm)

δ: 1.52 (6H, s), 2.78 (6H, s), 3.19 (2H, t, J=5.9 Hz), 3.51 (2H, q, J=5.8 Hz), 8.84 (1H, t, J=5.4 Hz).

Hereinafter, the constipation ameliorating action of the compound represented by the foregoing formula (I) is described by reference to Tests 1 and 2.

Test 1: Ameliorating Effect on Constipation Models Fed on Low-Fiber Diet

SD/IGS rats (6-wk old; CHARLES RIVER LABORATORIES JAPAN, INC.) in groups, each consisting of two heads per cage, were fed on a diet with a decreased dietary fiber content of 5% for a week in order to induce constipation. The normal group was fed on a standard diet with 15% dietary fiber (MF diet; ORIENTAL YEAST CO., LTD.) On the day before the test, each rat was measured for body weight and thereafter transferred into an individual cage. Grouping was performed on the basis of the body weights measured on the day before the test. The experimental groups of rats with induced constipation were orally administered compound (I) in a volume of 5 mL/kg body weight as dissolved in 0.5% (w/v) methylcellulose (MC), whereas the control vehicle group was orally administered 0.5% MC only. Compound (I) and 0.5% MC were also administered 8 hours after the first administration. Immediately after the first administration, a stool recovery tray was placed under each cage and starting 2 hours after the administration, stools were recovered every two hours until 24 hours after the administration; the appearance of the recovered stools was observed and their weight was measured. To determine their moisture content, the stools were measured for their wet weight, dried for at least 8 hours at 100° C., measured for dry weight, and its proportion (%) to the wet weight was calculated.

Figure 2:
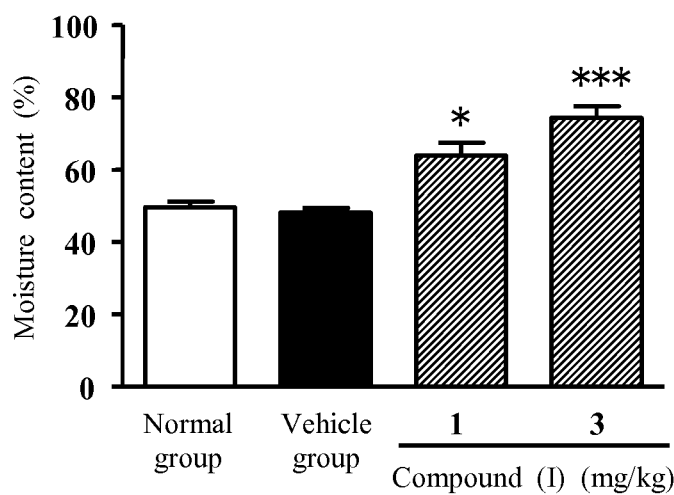
FIG. 2 is a diagram illustrating how well the constipation in rats as a constipation model was ameliorated (the moisture content of stools increased) as the result of administering the compound represented by formula (I).

The test results are depicted in FIGS. 1 and 2.

Upon administration of compound (I), both the wet weight of stools (FIG. 1) and the moisture content of stools (FIG. 2) from the constipation models increased. These results indicate that compound (I) is effective against constipation.

Test 2: Ameriolating Effect on Loperamide-Induced Constipation

The effects on constipation as induced by loperamide which suppresses the propulsion of the digestive tract's contents and the secretion of intestinal juice were investigated.

SD/IGS rats (6-wk old; CHARLES RIVER LABORATORIES JAPAN, INC.) in groups, each consisting of one head per cage, were kept in a day-and-night reversal room for 11 days. The rats were fasted for about 16 hours and orally administered 0.5% MC suspended loperamide at a dose of 5 mg/5 mL/kg body weight to prepare constipation models. The normal group was orally administered on 0.5% MC only. One hour after the administration of loperamide, the experimental groups were orally administered compound (I) in a volume of 5 mL/kg body weight as dissolved or suspended in 0.5% MC, whereas the control vehicle group was orally administered 0.5% MC only. At the same time, the normal group was also administered orally with 0.5% MC only. Loperamide was also administered to the experimental groups and the vehicle group 6 hours after the administration of compound (I). Immediately after the administration of compound (I), 5 g of a standard diet (MF diet; ORIENTAL YEAST CO., LTD.) was applied and thereafter, a stool recovery tray was placed under each cage and starting 2 hours after the administration, stools were recovered every two hours until after 12 hours; the appearance of the recovered stools was observed and their weight was measured. To determine their moisture content, the stools were measured for their wet weight, dried for at least 8 hours at 100° C., measured for dry weight, and its proportion (%) to the wet weight was calculated.

Figure 3:
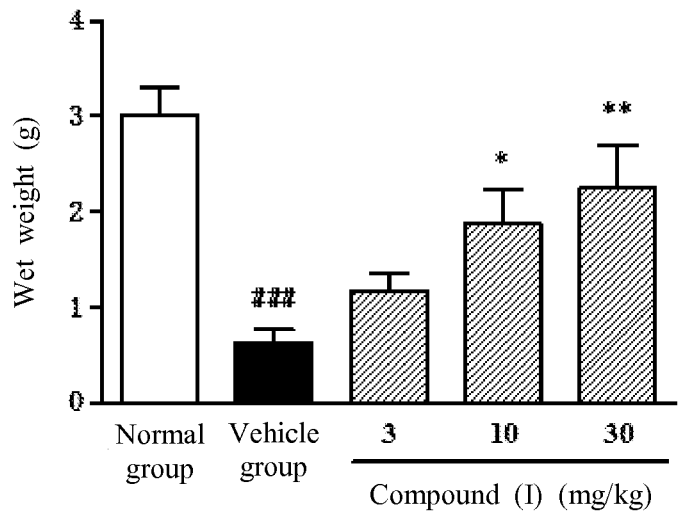
FIG. 3 is a diagram illustrating how well the constipation in rats as a constipation model was ameliorated (the wet weight of stools increased) as the result of administering the compound represented by formula (I).
Figure 4:
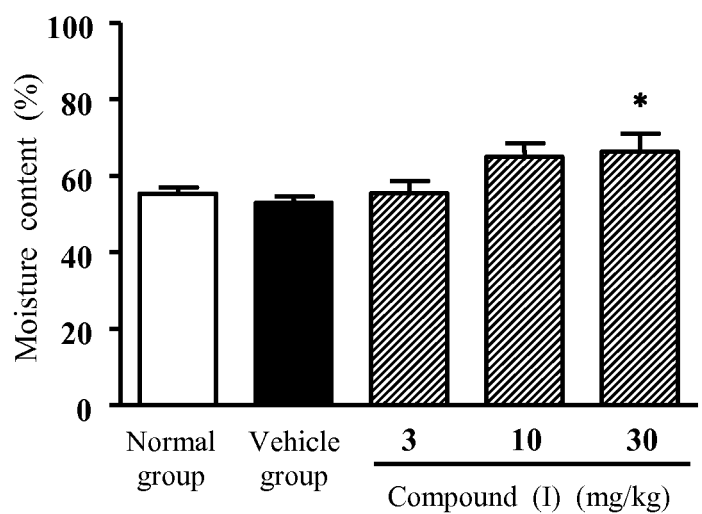
FIG. 4 is a diagram illustrating how well the constipation in rats as a constipation model was ameliorated (the moisture content of stools increased) as the result of administering the compound represented by formula (I).

The test results are depicted in FIGS. 3 and 4.

Upon administration of compound (I), both the wet weight of stools (FIG. 3) and the moisture content of stools (FIG. 4) from the constipation models increased. These results indicate that compound (I) is effective against constipation.

Hereinafter, the stability in the digestive tract of the compound represented by the foregoing formula (I) is described by reference to Test 3.

Test 3: Percentage of Compound (I) Remaining Unaltered in Rat's Digestive Tract

Seven-week old SD/IGS rats (CHARLES RIVER LABORATORIES JAPAN, INC.; male; fasted) were orally administered compound (I) (1 mg/kg) formulated with an aqueous solution of 0.5% CMC-Na (carboxymethylcellulose sodium salt). One, four and seven hours after the drug administration, the rats were euthanized under anesthetization with ether and their small intestine, cecum, and large intestine were removed. The contents of the small intestine were recovered by infusing the small intestine with 20 mL of physiological saline. After washing the tissue's surface with physiological saline, the tissues and the recovered contents were measured for their weight and homogenized under cooling with ice in the presence of added 4 volumes of purified water. The homogenate was deproteinated in the presence of an added acetonitrile/methanol solution containing an internal standard and, thereafter, the supernatant was analyzed by LC-MS/MS (Applied Biosystems: API3000). Drug-derived ions were detected by selected reaction monitoring based on electrospray ionization in a positive ion mode. From peak areas in the resulting extracted ion chromatogram, drug concentrations in the homogenate were calculated by the internal standard method.

The internal standard here used was compound 11 disclosed in WO2007/136116.

[Formula 17]

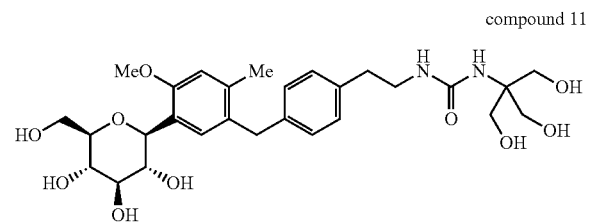

compound 11

The test results are shown in Table 1 below.

TABLE 1

Percentage of Compound (I) Remaining Unaltered in Rat's Digestive Tract (Relative to Dose)

| Drug | Time after dosing | Small intestine's contents | Small intestine | Cecum/large Intestine (including the contents) | Total |
|---|---|---|---|---|---|
| Compound (I) | 1 hr | 70.3 ± 6.7 | 4.9 ± 0.6 | 0.2 ± 0.3 | 75.4 ± 6.3 |
| | 4 hr | 69.7 ± 44.9 | 6.4 ± 5.3 | 33.1 ± 44.5 | 109.2 ± 10.7 |
| | 7 hr | 1.6 ± 1.2 | 0.7 ± 0.3 | 84.2 ± 8.8 | 86.5 ± 9.2 |

(Average of 4 cases ± S.D.)

Both 1 and 4 hours after the drug administration, about 75% of the dose remained unaltered in the small intestine and its contents (Table 1.)

Hereinafter, formulation examples of the prophylactic or therapeutic drug for constipation according to the present invention are described.

FORMULATION EXAMPLE 1

Granules containing the following ingredients are produced.

(Recipe)

| Ingredients | Compound represented by formula (I) | 10 mg |
|---|---|---|
| | Lactose | 700 mg |
| | Cornstarch | 274 mg |
| | HPC-L | 16 mg |
| | | 1000 mg |

(Method of Production)

The compound represented by formula (I) and lactose are passed through a 60-mesh sieve. The cornstarch is passed through a 120-mesh sieve. They are blended in a V-shape rotating mixer. To the powder mix, an aqueous solution of low-viscosity hydroxypropyl cellulose (HPC-L) is added and the mixture is kneaded, granulated (extruded through holes 0.5-1 mm in diameter) and dried. The resulting dry granules are passed through a vibrating sieve (12/60 mesh) to yield granules as a dosage form.

FORMULATION EXAMPLE 2

A capsule filling powder containing the following ingredients is produced.

| Ingredient | Compound represented by formula (I) | 10 mg |
|---|---|---|
| | Lactose | 79 mg |
| | Cornstarch | 10 mg |
| | Magnesium stearate | 1 mg |
| | | 100 mg |

(Method of Production)

The compound represented by formula (I) and lactose are passed through a 60-mesh sieve. The cornstarch is passed through a 120-mesh sieve. They are blended with the magnesium stearate in a V-shape rotating mixer. A 10× trituration of the powder (100 mg) is filled into No. 5 hard gelatin capsules.

FORMULATION EXAMPLE 3

A capsule filling powder containing the following ingredients is produced.

| Ingredient | Compound represented by formula (I) | 15 mg |
|---|---|---|
| | Lactose | 90 mg |
| | Cornstarch | 42 mg |
| | HPC-L | 3 mg |
| | | 150 mg |

(Method of Production)

The compound represented by formula (I) and lactose are passed through a 60-mesh sieve. The cornstarch is passed through a 120-mesh sieve. They are blended in a V-shape rotating mixer. To the powder mix, an aqueous solution of low-viscosity hydroxypropyl cellulose (HPC-L) is added and the mixture is kneaded, granulated and dried. The resulting dry granules are passed through a vibrating sieve (12/60 mesh) and regulated in size; 150 mg of the granules thus obtained are filled into No. 4 hard gelatin capsules.

FORMULATION EXAMPLE 4

Tablets containing the following ingredients are produced.

| Ingredients | Compound represented by formula (I) | 10 mg |
| --- | --- | --- |
| | Lactose | 90 mg |
| | Microcrystalline cellulose | 30 mg |
| | Magnesium stearate | 5 mg |
| | CMC-Na | 15 mg |
| | | 150 mg |

(Method of Production)

The compound represented by formula (I), lactose, microcrystalline cellulose, and CMC-Na (carboxymethylcellulose sodium salt) are passed through a 60-mesh sieve and mixed together. To the powder mix, the magnesium stearate is added to prepare a formulating powder mix. Direct compression of this powder mix yields tablets each weighing 150 mg.

INDUSTRIAL APPLICABILITY

The prophylactic or therapeutic drugs for constipation according to the present invention which comprise SGLT1 inhibiting compounds have a superior action for ameliorating constipation. Hence, the present invention enables the provision of pharmaceuticals that are effective for preventing or treating constipation, which is expected to contribute a further advance in the pharmaceutical industry.

The invention claimed is:

1. A method for treating constipation, which comprises administering a 4-isopropylphenyl glucitol compound represented by the following formula (I):

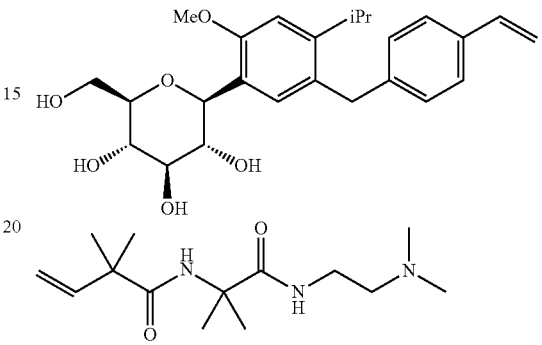

or a pharmaceutically acceptable salt thereof to a patient in need thereof.

2. The method according to claim 1, wherein the compound is administered orally.

* * * * *

UNITED STATES PATENT AND TRADEMARK OFFICE
CERTIFICATE OF CORRECTION

PATENT NO. : 10,022,389 B2  
APPLICATION NO. : 14/765134  
DATED : July 17, 2018  
INVENTOR(S) : Daisuke Yamamoto et al.

Page 1 of 2

It is certified that error appears in the above-identified patent and that said Letters Patent is hereby corrected as shown below:

Column 15, Lines 46-58, delete the structure:

"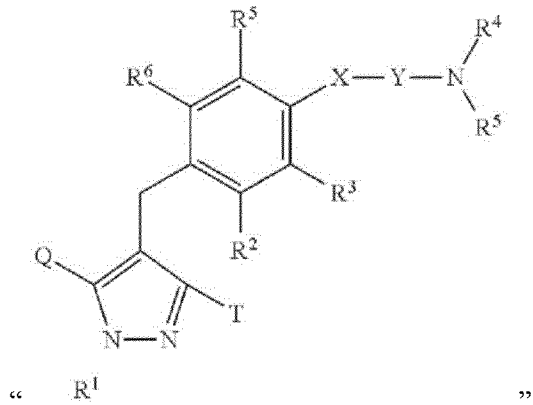"

And insert therefor:

--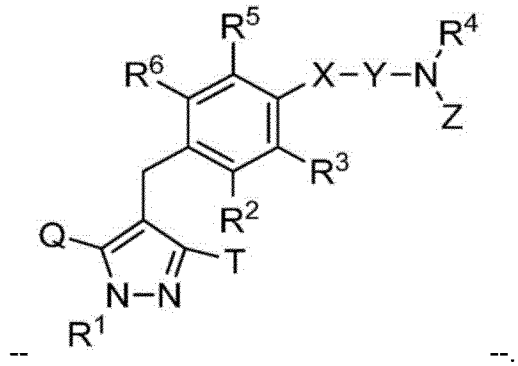--.

Signed and Sealed this  
Fifth Day of February, 2019

Andrei Iancu  
*Director of the United States Patent and Trademark Office*

CERTIFICATE OF CORRECTION (continued)
U.S. Pat. No. 10,022,389 B2

Column 31, Lines 40-46, delete the structure:

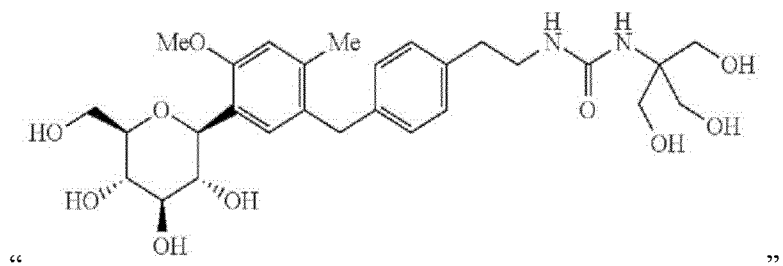
"                                                                 "

And insert therefor:

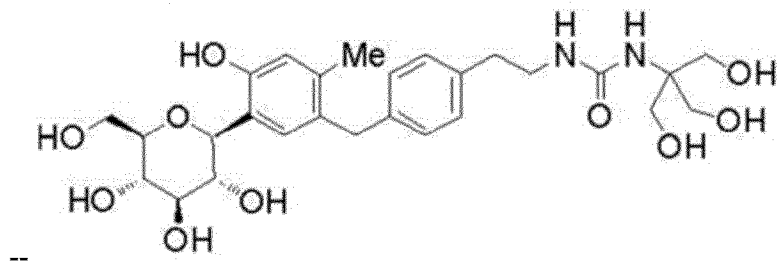
--                                                                --.

Claim 1, Column 34, Lines 11-25, delete the structure:

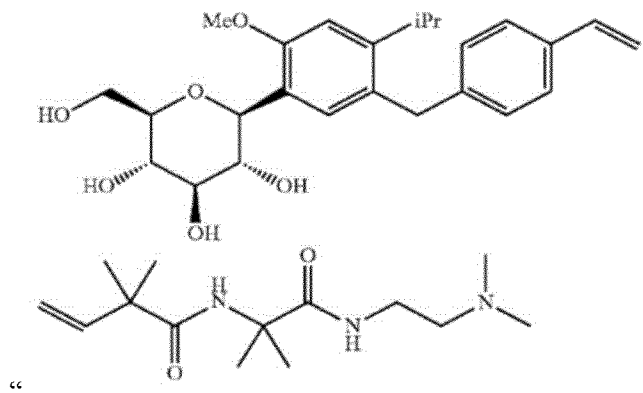
"                                                                 "

And insert therefor:

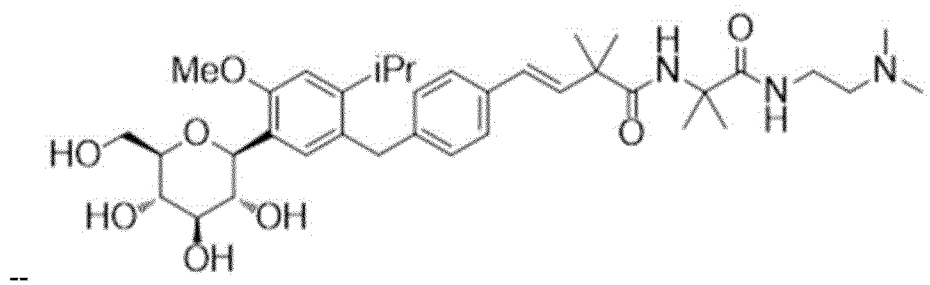
--                                                                --.